United States Patent
Beadle et al.

(10) Patent No.: US 11,833,014 B2
(45) Date of Patent: Dec. 5, 2023

(54) MULTIPLE DRESSING NEGATIVE PRESSURE WOUND THERAPY SYSTEM

(71) Applicant: T.J.Smith and Nephew, Limited, Hull (GB)

(72) Inventors: Victoria Beadle, Hull (GB); Sarah Jenny Collinson, Hull (GB); Mark Ellerington, Hull (GB); Yeswanth Gadde, Pocklington (GB); Edward Yerbury Hartwell, Hull (GB); William Kelbie, Inverness (GB); Natasha Rose Middleton, Hull (GB); Samuel John Mortimer, Kingston upon Hull (GB); Stephanie Jane Noble, Hull (GB); Gareth Walker, Hull (GB); Fraser George Weedon, Hull (GB); Jessica Winks, North Ferriby (GB)

(73) Assignee: T.J.Smith and Nephew, Limited, Hull (GB)

(*) Notice: Subject to any disclaimer, the term of this patent is extended or adjusted under 35 U.S.C. 154(b) by 179 days.

(21) Appl. No.: 17/498,501

(22) Filed: Oct. 11, 2021

(65) Prior Publication Data

US 2022/0023527 A1 Jan. 27, 2022

Related U.S. Application Data

(62) Division of application No. 16/489,323, filed as application No. PCT/EP2018/054812 on Feb. 27, 2018, now Pat. No. 11,141,521.

(Continued)

(51) Int. Cl.
| | | |
|---|---|---|
| A61F 13/00 | (2006.01) | |
| A61F 13/02 | (2006.01) | |
| A61M 1/00 | (2006.01) | |

(52) U.S. Cl.
CPC .... *A61F 13/00068* (2013.01); *A61F 13/0216* (2013.01); *A61M 1/734* (2021.05);
(Continued)

(58) Field of Classification Search
CPC .......... A61F 13/00068; A61F 13/0216; A61M 1/734; A61M 1/743; A61M 1/915;
(Continued)

(56) References Cited

U.S. PATENT DOCUMENTS

| | | |
|---|---|---|
| 5,960,795 A | 10/1999 | Schultz |
| 7,438,705 B2 | 10/2008 | Karpowicz et al. |

(Continued)

FOREIGN PATENT DOCUMENTS

| | | |
|---|---|---|
| CN | 1688948 A | 10/2005 |
| CN | 202822419 U | 3/2013 |

(Continued)

OTHER PUBLICATIONS

International Preliminary Report on Patentability for Application No. PCT/EP2018/054812, dated May 29, 2019, 63 pages.
(Continued)

*Primary Examiner* — Susan S Su
*Assistant Examiner* — Eric Rassavong
(74) *Attorney, Agent, or Firm* — Knobbe, Martens, Olson & Bear, LLP

(57) ABSTRACT

Embodiments described herein relate to apparatuses, systems, and methods for the treatment of wounds, for example using multiple wound dressings in combination with negative pressure wound therapy. A negative pressure would therapy apparatus can include a negative pressure source and a controller. The negative pressure source can include inlets configured to couple via fluid flow paths to wound dressings. The fluid flow paths can include pressure sensors configured to measure pressure in the fluid flow paths. The pressure (Continued)

sensors can include a first pressure sensor configured to measure pressure in the first fluid flow path and a second pressure sensor configured to measure pressure in the second fluid flow path. The controller can be configured to operate the negative pressure source and provide, based on measured pressure, indication of at least one operating condition associated with at least one of the fluid flow paths.

20 Claims, 23 Drawing Sheets

Related U.S. Application Data

(60) Provisional application No. 62/465,011, filed on Feb. 28, 2017, provisional application No. 62/464,992, filed on Feb. 28, 2017, provisional application No. 62/464,988, filed on Feb. 28, 2017.

(52) U.S. Cl.
CPC ............ *A61M 1/743* (2021.05); *A61M 1/915* (2021.05); *A61M 1/96* (2021.05); *A61M 1/985* (2021.05); *A61M 1/913* (2021.05); *A61M 1/962* (2021.05); *A61M 1/982* (2021.05); *A61M 2205/15* (2013.01); *A61M 2205/18* (2013.01); *A61M 2205/3334* (2013.01); *A61M 2205/3344* (2013.01); *A61M 2205/3569* (2013.01); *A61M 2205/50* (2013.01); *A61M 2205/581* (2013.01); *A61M 2205/587* (2013.01); *A61M 2205/6054* (2013.01); *A61M 2205/6063* (2013.01); *A61M 2205/6081* (2013.01); *A61M 2205/7518* (2013.01); *A61M 2205/7536* (2013.01)

(58) Field of Classification Search
CPC ........ A61M 1/96; A61M 1/985; A61M 1/913; A61M 1/962; A61M 1/982; A61M 2205/15; A61M 2205/18; A61M 2205/3334; A61M 2205/3344; A61M 2205/3569; A61M 2205/50; A61M 2205/581

See application file for complete search history.

(56) References Cited

U.S. PATENT DOCUMENTS

| | | | |
|---|---|---|---|
| 7,945,302 B2 | 5/2011 | McAdams | |
| 8,682,442 B2 | 3/2014 | McAdams | |
| 8,974,429 B2 | 3/2015 | Gordon et al. | |
| 9,526,439 B2 | 12/2016 | Connelly et al. | |
| 9,526,920 B2 * | 12/2016 | Tanis | A61B 5/1172 |
| 10,155,070 B2 | 12/2018 | Childress et al. | |
| 2005/0004501 A1 | 1/2005 | Lorenzo | |
| 2008/0200096 A1 | 8/2008 | Thornton et al. | |
| 2010/0268111 A1 | 10/2010 | Drinan et al. | |
| 2011/0313339 A1 | 12/2011 | Vitaris et al. | |
| 2012/0123358 A1 | 5/2012 | Hall et al. | |
| 2012/0136325 A1 | 5/2012 | Allen et al. | |
| 2012/0190956 A1 | 7/2012 | Connolly | |
| 2012/0209226 A1 | 8/2012 | Simmons et al. | |
| 2013/0110058 A1 * | 5/2013 | Adie | A61M 1/74 604/319 |
| 2013/0131616 A1 | 5/2013 | Locke | |
| 2013/0144227 A1 | 6/2013 | Locke et al. | |
| 2013/0150813 A1 | 6/2013 | Gordon et al. | |
| 2014/0228789 A1 | 8/2014 | Wilkes et al. | |
| 2014/0350494 A1 | 11/2014 | Hartwell et al. | |
| 2015/0231021 A1 | 8/2015 | Smith et al. | |
| 2016/0045377 A1 | 2/2016 | Robinson et al. | |
| 2016/0081580 A1 | 3/2016 | Bergelin et al. | |
| 2016/0101282 A1 | 4/2016 | Bergelin et al. | |
| 2016/0120706 A1 | 5/2016 | Collinson et al. | |
| 2016/0287763 A1 | 10/2016 | Simmons et al. | |
| 2017/0014560 A1 * | 1/2017 | Minskoff | A61M 1/734 |
| 2017/0028111 A1 | 2/2017 | Tumey et al. | |
| 2017/0156658 A1 | 6/2017 | Maharbiz et al. | |
| 2017/0368239 A1 | 12/2017 | Askem et al. | |
| 2018/0055359 A1 | 3/2018 | Shamim et al. | |
| 2018/0168916 A1 | 6/2018 | Kelch et al. | |
| 2019/0290499 A1 | 9/2019 | Askem et al. | |

FOREIGN PATENT DOCUMENTS

| | | |
|---|---|---|
| CN | 103585682 A | 2/2014 |
| CN | 104066900 A | 9/2014 |
| CN | 204670041 U | 9/2015 |
| JP | 2014237992 A | 12/2014 |
| JP | 2016118204 A | 6/2016 |
| WO | WO-2011135286 A1 | 11/2011 |
| WO | WO-2012021553 A1 | 2/2012 |
| WO | WO-2013171585 A2 | 11/2013 |
| WO | WO-2015168720 A1 | 11/2015 |
| WO | WO-2016018448 A1 | 2/2016 |
| WO | WO-2016109041 A1 | 7/2016 |
| WO | WO-2017197357 A1 | 11/2017 |
| WO | WO-2018041854 A1 | 3/2018 |
| WO | WO-2018158250 A1 | 9/2018 |
| WO | WO-2018167199 A1 | 9/2018 |
| WO | WO-2018212849 A1 | 11/2018 |
| WO | WO-2019020551 A1 | 1/2019 |

OTHER PUBLICATIONS

International Search Report and Written Opinion for Application No. PCT/EP2018/054812, dated Jul. 11, 2018, 14 pages.

Invitation to Pay Additional Fees and Partial Search Report for Application No. PCT/EP2018/054812, dated May 18, 2018, 13 pages.

KCI, "V.A.C. Therapy Clinical guidelines: A reference source for clinicians," Nov. 2005, 24 pages.

Written Opinion of the International Preliminary Examining Authority for Application No. PCT/EP2018/054812, dated Feb. 21, 2019, 8 pages.

* cited by examiner

Before Negative Pressure

During Negative Pressure

MULTIPLE DRESSING NEGATIVE PRESSURE WOUND THERAPY SYSTEM

RELATED APPLICATIONS

This application is a divisional application of U.S. application Ser. No. 16/489,323, filed Aug. 27, 2019, which is a national stage application of International Patent Application No. PCT/EP2018/054812, filed Feb. 27, 2018, which claims priority to U.S. Provisional Application No. 62/464,988, filed Feb. 28, 2017, entitled "MULTIPLE DRESSING NEGATIVE PRESSURE WOUND THERAPY SYSTEM," U.S. Provisional Application No. 62/464,992, filed Feb. 28, 2017, entitled "MULTIPLE DRESSING NEGATIVE PRESSURE WOUND THERAPY SYSTEM," and U.S. Provisional Application No. 62/465,011, filed Feb. 28, 2017, entitled "MULTIPLE DRESSING NEGATIVE PRESSURE WOUND THERAPY SYSTEM," each of which is hereby incorporated by reference in its entirety.

BACKGROUND

Technical Field

Embodiments described herein relate to apparatuses, systems, and methods for the treatment of wounds, for example using multiple wound dressings in combination with negative pressure wound therapy.

Description of the Related Art

Negative pressure wound therapy (NPWT) promotes wound healing by facilitating the formation of granulation tissue at the wound site and by assisting the body's normal inflammatory process while simultaneously removing excess fluid, which may contain adverse cytokines and/or bacteria. However, existing NPWT systems are typically limited at least because they are able to treat only one wound at a time. When existing NPWT systems are used for treating more than one wound, this results in ineffective and imprecise treatment. Accordingly, further improvements in NPWT are needed to fully realize the benefits of treatment.

SUMMARY

In some embodiments, a negative pressure would therapy apparatus includes a negative pressure source, a plurality of pressure sensors, and a controller. The negative pressure source includes a plurality of inlets configured to couple via a plurality of fluid flow paths to a plurality of wound dressings and provide negative pressure to the plurality of wound dressings. The plurality of fluid flow paths include a first fluid flow path configured to fluidically connect a first wound dressing to a first inlet of the plurality of inlets, and a second fluid flow path configured to fluidically connect a second wound dressing to a second inlet of the plurality of inlets. The plurality of pressure sensors are configured to measure pressure in the plurality of fluid flow paths. The plurality of pressure sensors include a first pressure sensor configured to measure pressure in the first fluid flow path, and a second pressure sensor configured to measure pressure in the second fluid flow path. The controller is configured to operate the negative pressure source and provide, based on pressure measured by at least one of the first or second pressure sensors, indication of at least one operating condition associated with at least one of the first or second fluid flow paths.

The apparatus of the preceding paragraph may also include any combination of the following features described in this paragraph, among others described herein. At least one operating condition can include a blockage, a leakage, an overpressure, or a dressing full condition. The apparatus can further include a housing configured to support the negative pressure source and the first and second inlets. The first fluid flow path can include a first identifier configured to indicate to a user a fluidic connection between the first wound dressing and the negative pressure source. The second fluid flow path can include a second identifier configured to indicate to the user a fluidic connection between the second wound dressing and the negative pressure source. The first and second identifiers can include at least one of a printed glyph, a printed icon, an embossed glyph, an embossed icon, a braille character, or a color coding. The first and second identifiers can be positioned proximate the inlet manifold branching attachment. The controller can be further configured to provide a first indication associated with an operating condition in the first fluid flow path and a second indication associated with an operating condition in the second fluid flow path. The first and second indications can be one or more of visual or audio indications.

In some embodiments, a negative pressure wound therapy apparatus can include a negative pressure source, a pressure sensor, and a controller. The negative pressure source can include a plurality of inlets configured to be coupled via a plurality of fluid flow paths to a plurality of wound dressings and provide negative pressure to the plurality of wound dressings. The plurality of fluid flow paths can include a first fluid flow path configured to fluidically connect a first wound dressing to a first inlet of the plurality of inlets and a second fluid flow path configured to fluidically connect a second wound dressing to a second inlet of the plurality of inlets. The first fluid flow path can include a flow restrictor or a flow enlarger. a pressure sensor configured to measure pressure in at least one of the plurality of fluid flow paths. The controller can be configured to operate the negative pressure source and provide, based on pressure measured by the pressure sensor, indication of at least one operating condition associated with at least one of the first or second fluid flow paths.

The apparatus of the preceding paragraph may also include any combination of the following features described in this paragraph, among others described herein. The at least one operating condition can include one or more of a blockage, a leakage, an overpressure, or a dressing full condition. The controller can be configured to provide the indication of the at least one operating condition based on pressure changes over time. Pressure changes over time in the first fluid flow path can be different from pressure changes over time in the second fluid flow path. The controller can be further configured to detect a blockage in the first or second fluid flow path based on the difference in the pressure changes over time in the first and second fluid flow paths. The apparatus can further include a housing configured to support the negative pressure source and the first and second inlets. The first fluid flow path can include a first identifier configured to indicate to a user a fluidic connection between the first wound dressing and the negative pressure source. The second fluid flow path can include a second identifier configured to indicate to the user a fluidic connection between the second wound dressing and the negative pressure source. The first and second identifiers can include at least one of a printed glyph, a printed icon, an embossed glyph, an embossed icon, a braille character, or a color coding. The controller can be further configured to provide a first indication associated with an operating condition in the first fluid flow path and a second indication associated with an operating condition in the second fluid flow path. The first and second indications can be one or more of visual or audio indications.

In some embodiments, a negative pressure therapy apparatus can include a negative pressure source, a pressure sensor and a controller. The negative pressure source can be configured to couple via a plurality of fluid flow paths to a plurality of wound dressings and provide negative pressure to the plurality of wound dressings. The plurality of fluid flow paths can include a first fluid flow path and a second fluid flow path. The first fluid flow path can be configured to fluidically connect a first wound dressing to the negative pressure source The first fluid flow path can have a first valve configured to block passage of fluid in the first fluid flow path. The second fluid flow path can be configured to fluidically connect a second wound dressing to the negative pressure source. The second fluid flow path can have a second valve configured to block passage of fluid in the second fluid flow path. The pressure sensor can be configured to measure pressure in the plurality of fluid flow paths. The controller can be configured to operate the negative pressure source and to detect an operating condition associated with at least one of the first or second fluid paths based on the measured pressure.

The apparatus of the preceding paragraph may also include any combination of the following features described in this paragraph, among others described herein. The controller can be configured to detect an operating condition in the first fluid flow path when the first valve is open to allow passage of fluid in the first fluid flow path and the second valve is closed to block passage of fluid in the second fluid flow path. The operating condition in the first fluid flow path can include blockage in the first fluid flow path. The plurality of fluid flow paths further can include a third fluid flow path configured to fluidically connect a third wound dressing to the negative pressure source. The third fluid flow path can include a third valve configured to block passage of fluid in the third fluid flow path. The controller can be configured to detect an operating condition in the first fluid flow path when the first valve is open to allow passage of fluid in the first fluid flow path, the second valve is closed to block passage of fluid in the second fluid flow path, and the third valve is closed to block passage of fluid in the third fluid flow path.

The apparatus of any of the two preceding paragraphs may also include any combination of the following features described in this paragraph, among others described herein. The controller can be further configured to close the first valve to block passage of fluid in the first fluid flow path, close the second valve to block passage of fluid in the second fluid flow path, open the third valve to allow passage of fluid in the third fluid flow path, based on comparing the measured pressure to a first threshold, determine presence of a blockage in the third fluid flow path, and in response to determining that the blockage is present in the third fluid flow path, provide indication of the blockage to a user. The controller can be further configured to in response to determining blockage in the third fluid flow path open the first valve to allow passage of fluid in the first fluid flow path, open the second valve to allow passage of fluid in the second fluid flow path, close the third valve to block passage of fluid in the third fluid flow path, based on comparing the measured pressure to a second threshold, determine presence of a blockage in one or more of the first and second fluid flow paths, and in response to determining that the blockage is not present in the first and second fluid flow paths, provide indication to replace the third wound dressing. The controller is further configured to, in response to determining that the blockage is present in at least one of the first or second fluid flow paths, provide indication of the blockage to the user.

In some embodiments, a method of operating a negative pressure wound therapy device includes closing a first valve associated with a first fluid flow path. The first fluid flow path can be configured to provide fluidic connection between a negative pressure source and a first wound dressing. Closing the first valve can block flow of fluid in the first fluid flow path. The method can further include opening a second valve associated with a second fluid flow path. The second fluid flow path can be configured to provide fluidic connection between the negative pressure source and a second wound dressing. Opening the second valve can allow flow of fluid in the second fluid flow path. The method can further include determining an operating condition associated with the second fluid flow path based at least in part on a measured pressure in the second fluid flow path. The method can further include providing indication of the operating condition.

The method of the preceding paragraph may also include any combination of the following features or steps described in this paragraph, among others described herein. The operating condition associated with the second fluid flow path can include blockage in the second fluid flow path. The method can further include, in response to determining blockage in the second fluid flow path, closing the second valve and opening the first valve; and providing an indication to replace the second dressing. The method can further include determining an operating condition associated with the first fluid flow path. The method can further include a third fluid flow path configured to provide fluidic connection between the negative pressure source and a third wound dressing. The third fluid flow path can include a third valve configured to provide fluidic connection between the negative pressure source and the third wound dressing. Closing the third valve blocks flow of fluid in the third fluid flow path.

In some embodiments, a method of operating a negative pressure wound therapy device includes opening a first valve associated with a first fluid flow path. The first fluid flow path can be configured to provide fluidic connection between a negative pressure source and a first wound dressing. Closing the first valve blocks fluid flow in the first fluid flow path. The method can further include closing a second valve associated with a second fluid flow path. The second fluid flow path can be configured to provide fluidic connection between the negative pressure source and a second wound dressing. Opening the second valve allows fluid flow in the second fluid flow path. The method can further include closing a third valve associated with a third fluid flow path. The third fluid flow path can be configured to provide fluidic connection from a negative pressure source to a third wound dressing. Closing the third valve blocks fluid flow in the third fluid flow path. The method can further include determining presence of a blockage in the first fluid flow path based at least in part on a measured pressure in the first fluid flow path. The method can further include upon a determination of the blockage in the first fluid flow path, closing the first valve (e.g., closing the first valve blocks the flow of fluid in the first fluid flow path), opening the second and third valves (e.g., opening the second and third valves allows flow of fluid in the second and third fluid flow paths), determining presence of a blockage in at least one of the second or third fluid flow paths, in response to determining that there is no blockage in the second and third fluid flow paths, providing an indication to a user to replace the first wound dressing, and in response to determining that there is blockage in at least one of the second or third fluid flow paths, provide indication to the user.

In some embodiments, a negative pressure therapy apparatus can include a wound dressing. The wound dressing can include a substantially stretchable wound contact layer including a wound facing side and a non-wound facing side opposite the wound facing side. The wound facing side of the wound contact layer can be configured to be positioned in contact with a wound. The wound facing side of the wound contact layer can support a plurality of electronic components and a plurality of electronic connections that connect at least some of the plurality of the electronic components. The wound facing side of the wound contact layer can include a first region of substantially non-stretchable material that supports at least one electronic component from the plurality of electronic components. The at least one electronic component can be attached to the first region of substantially non-stretchable material with adhesive material.

The apparatus of the preceding paragraph may also include any combination of the following features described in this paragraph, among others described herein. The wound facing side of the wound contact layer can include a second region of substantially non-stretchable material that supports at least one electronic connection from the plurality of electronic connections. The wound contact layer can include a substrate supporting the plurality of electronic components and the plurality of electronic connections and a conformal coating covering at least the plurality of electronic components and the plurality of electronic connections. The conformal coating can be configured to prevent fluid from coming into contact with the plurality of electronic components and the plurality of electronic connections. The substrate can be formed from thermoplastic polyurethane and the conformal coating is formed from urethane. The wound contact layer can include a plurality of perforations configured to allow fluid to pass through the wound contact layer when negative pressure is applied to the wound. The plurality of perforations can be further configured to allow substantially unidirectional flow of fluid through the wound contact layer to prevent fluid removed from the wound from flowing back toward the wound.

The apparatus of any of the two preceding paragraphs may also include any combination of the following features described in this paragraph, among others described herein. The wound facing side of the wound contact layer can include a region of additional adhesive material configured to position the at least one electronic component in the wound. The wound facing side of the wound contact layer can include a third region of substantially non-stretchable material that encloses the at least one electronic component. The at least one electronic component can include one or more of a sensor, a light emitter, a processor, or a communications controller. The plurality of electronic connections can include a plurality of electrical traces. The apparatus can further include a negative pressure source configured to be fluidically connected to the wound dressing. The wound dressing can further include an absorbent layer positioned over the non-wound facing side of the wound contact layer and a backing layer positioned over the absorbent layer. The wound contact layer can be sealed to the backing layer. The apparatus can further include a port on the backing layer. The port can be configured to fluidically connect the wound dressing to a negative pressure source. The adhesive material can be thermally curable.

The apparatus of any of the preceding paragraphs may also include any combination of the following features described in this paragraph, among others described herein. The apparatus can further include an indicator configured to alert a user to check at least one of the plurality of wound dressings; a processor configured to periodically activate the indicator; and a button configured permit the user to reset the alert for the user to check at least one of the plurality of wound dressings.

In some embodiments, a method of manufacturing a wound dressing includes providing a substantially stretchable wound contact layer including a wound facing side and a non-wound facing side opposite the wound facing side. The wound facing side of the wound contact layer can be configured to be positioned in contact with a wound. The method can further include positioning a first region of substantially non-stretchable material on the wound facing side of the wound contact layer and positioning a plurality of electronic components and a plurality of electronic connections on the wound facing side of the wound contact layer. The at least one electronic component from the plurality of electronic components can be supported by the first region of substantially non-stretchable material, and at least one electronic component can be attached to the first region of substantially non-stretchable material with adhesive material.

The method of the preceding paragraph may also include any combination of the following features or steps described in this paragraph, among others described herein. The wound contact layer can include a substrate. The method can further include perforating the substrate around the plurality of electronic components and the plurality of electronic connections; and applying conformal coating over at least the plurality of electronic components and the plurality of electronic connections. The conformal coating can be configured to prevent fluid from coming into contact with the plurality of electronic components and the plurality of electronic connections. The method can further include identifying a plurality of locations of the plurality of electronic components and the plurality of electronic connections on the substrate prior to perforating the substrate around the plurality of electronic components and the plurality of electronic connections. Identifying the plurality of locations can include identifying one or more of: a location of an RFID chip or antenna positioned on the substrate or a location of an electronic connection configured to be connected to an electronic component external to the substrate.

The method of any of the two preceding paragraphs may also include any combination of the following features or steps described in this paragraph, among others described herein. The method can further include applying a region of additional adhesive material to the wound facing side of the wound contact layer. The additional adhesive material can be configured to position the at least one electronic component in the wound. The method can further include identifying a location of the at least one electronic component prior to applying the region of additional adhesive material. The wound contact layer can include a substrate. The method can further include applying conformal coating over at least the plurality of electronic components and the plurality of electronic connections. The conformal coating can be configured to prevent fluid from coming into contact with the plurality of electronic components and the plurality of electronic connections. The method can further include applying a region of adhesive material to the wound facing side of the wound contact layer, the adhesive material configured to position the at least one electronic component in the wound; and perforating the substrate around the plurality of electronic components and the plurality of electronic connections. The method can further include identifying a plurality of locations of the plurality of electronic components and the plurality of electronic connections on the substrate prior to perforating the substrate around the plurality of electronic components and the plurality of electronic connections.

The method of any of the three preceding paragraphs may also include any combination of the following features or steps described in this paragraph, among others described herein. The method can further include identifying a location of the at least one electronic component prior to applying the region of adhesive material. Identifying the plurality of locations can include identifying one or more of: a location of an RFID chip or antenna positioned on the substrate or a location of an electronic connection configured to be connected to an electronic component external to the substrate. The method can further include positioning a second region of substantially non-stretchable material on the wound facing side of the wound contact layer; and supporting at least one electronic connection from the plurality of electronic connections on the second region. The method can further include enclosing the at least one electronic component by a third region of substantially non-stretchable material positioned on the wound facing side of the wound contact layer. The method can further include cutting the wound contact layer along at least one cutting line to separate a region of the wound contact layer including the plurality of electronic components and the plurality of electronic connections; and attaching the region of the wound contact layer to one or more of an absorbent layer or a backing layer to form a wound dressing. The substrate can be formed thermoplastic polyurethane and the conformal coating is formed from urethane. The adhesive material can be thermally curable.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

DETAILED DESCRIPTION

Figure 1:
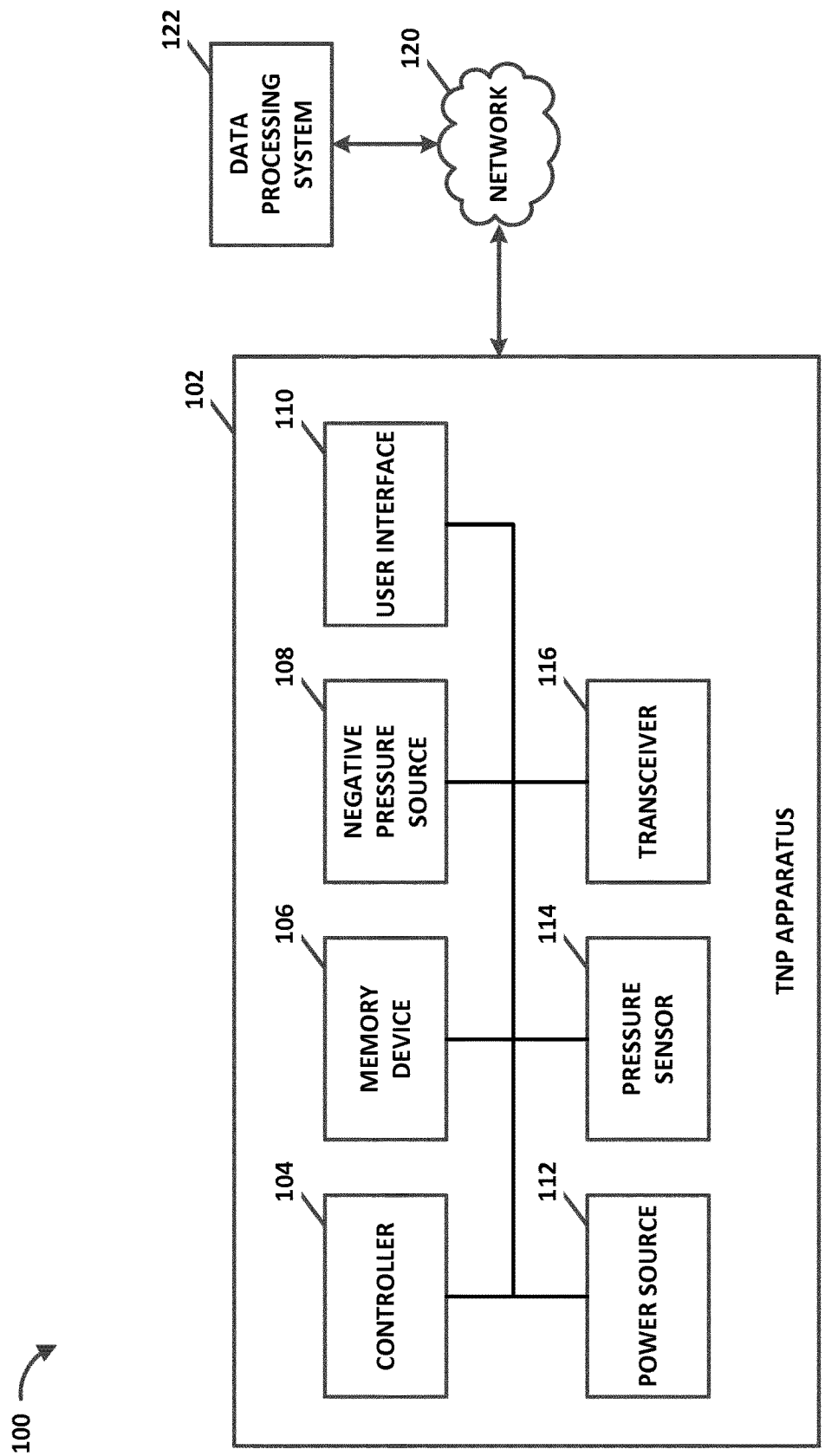
FIG. 1 illustrates a negative pressure therapy system that includes a TNP apparatus and a remote data processing system according to some embodiments.

Embodiments disclosed herein relate to apparatuses and methods of treating a plurality of wounds with reduced pressure, including a source of negative pressure and wound dressing components and apparatuses. The apparatuses and components including a wound overlay and packing materials, if any, may collectively be referred to as dressings.

Embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure (TNP) therapy systems. Briefly, negative pressure wound therapy assists in the closure and healing of many forms of "hard to heal" wounds by reducing tissue oedema;

encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of, for example, −X mmHg reflects pressure that is X mmHg below 760 mmHg or, in other words, a pressure of (760-X) mmHg. In addition, negative pressure that is "less" or "smaller" than X mmHg may correspond to pressure that is closer to atmospheric pressure (such as, −40 mmHg is less than −60 mmHg). Negative pressure that is "more" or "greater" than −X mmHg may correspond to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments, a pressure range of below −75 mmHg can be used. Alternatively, the negative pressure apparatus can supply a pressure range of over approximately −100 mmHg, or even −150 mmHg.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (such as, heartbeat).

FIG. 1 illustrates a negative pressure therapy system 100 that includes a TNP apparatus 102 and a remote data processing system 122 according to some embodiments. The TNP apparatus 102 can be used to treat a wound using a wound dressing that is in fluidic communication with the TNP apparatus 102 via a fluid flow path. The TNP apparatus 102 can include a controller 104, a memory device 106, a negative pressure source 108, a user interface 110, a power source 112, a pressure sensor 114, and a transceiver 116 that are configured to electrically communicate with one another. The power source 112 can provide power to one or more components of the TNP apparatus 102.

The controller 104 can control operations of one or more other components of the TNP apparatus 102 according at least to instructions stored in the memory device 106. The controller 104 can, for instance, control operations of and supply of negative pressure by the negative pressure source 108. The negative pressure source 108 can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing. The user interface 110 can include one or more elements that receive user inputs or provide user outputs to a patient or caregiver. The one or more elements that receive user inputs can include buttons, switches, dials, touch screens, or the like.

The pressure sensor 114 can be used to monitor pressure underneath a wound dressing, such as (i) pressure in a fluid flow path connecting the TNP apparatus 102 and the wound dressing, (ii) pressure at the wound dressing, or (iii) pressure at or in the TNP apparatus 102. In some implementations, the pressure sensor 114 can include at least two or more pressure sensors that are positioned to measure the pressure of multiple fluid flow paths, such as multiple flow paths connecting the TNP apparatus 102 to multiple wound dressings. On other implementations, the pressure sensor 114 can include at least two or more pressure sensors that are positioned in or fluidically connected to the fluid flow path to permit differential measurement of the pressure. For example, a first pressure sensor can be positioned upstream of the wound (such as at or near the inlet of the TNP apparatus 102) and a second pressure sensor can be positioned to detect pressure at or near the wound or at or near a canister or dressing.

The transceiver 116 can be used to communicate with the data processing system 122 via a network 120. The transceiver 116 can, for example, transmit device usage data like alarms, measured pressure, or changes to a therapy program administered by the TNP apparatus 102 to the data processing system 122. In some examples, the transceiver 116 communicate with one or more shut-off valves in a negative pressure therapy system. The network 120 can be a communication network, such as a wired or wireless communications network (for example, a cellular communications network). The memory device 106 can be used to store the device usage data that may be transmitted by the transceiver 116. In some embodiments, the data processing system 122 can transmit data, such as operating parameters, to the TNP apparatus 102.

Figure 2:
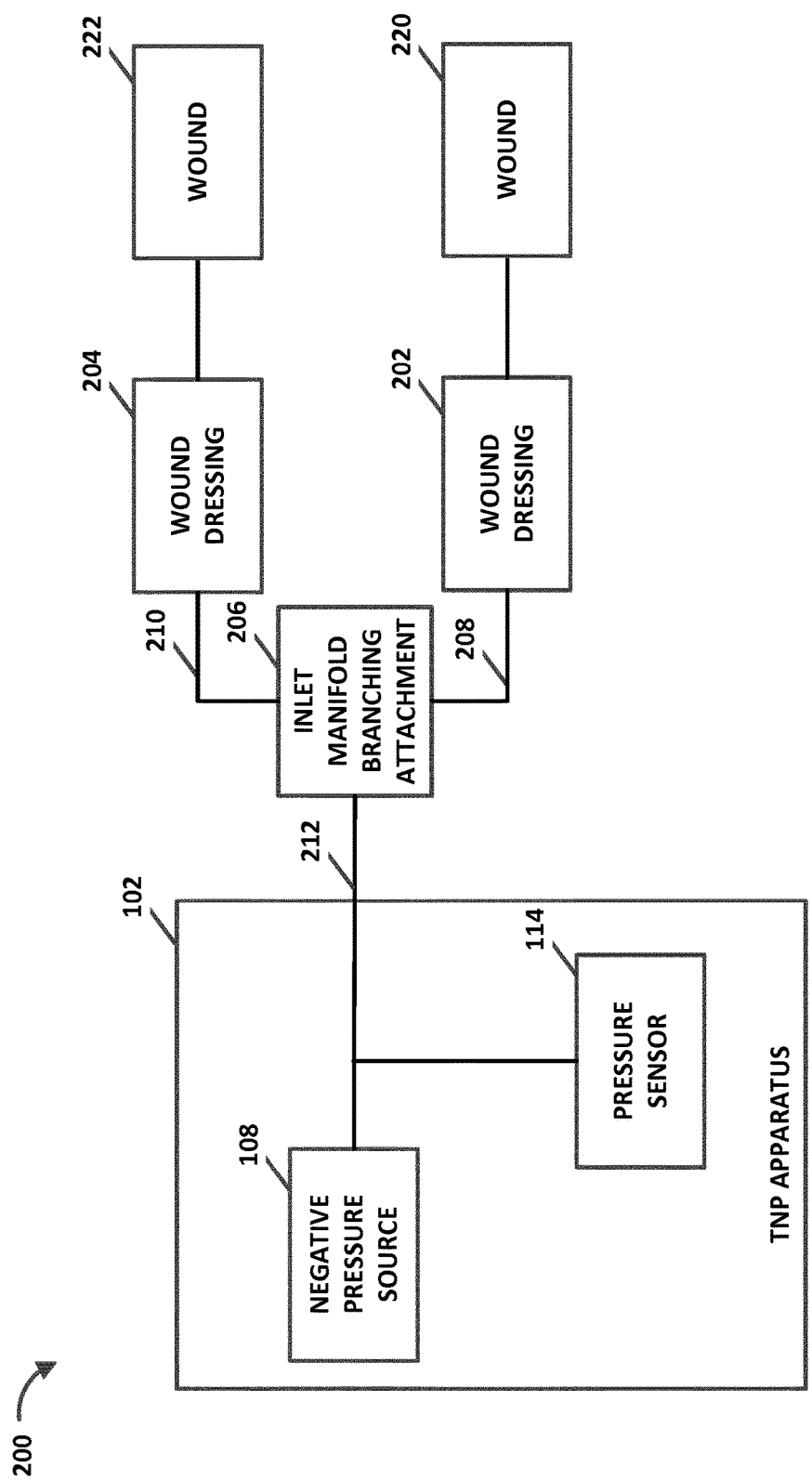
FIG. 2 illustrates a negative pressure therapy system that includes the TNP apparatus of FIG. 1, as well as an inlet manifold branching attachment, pressure sensor and a plurality of fluid flow paths, wound dressings positioned over wounds according to some embodiments.

FIG. 2 illustrates a negative pressure therapy system 200 according to some embodiments. The system 200 includes the TNP apparatus 102 of FIG. 1, as well as a first fluid flow path 208, a first wound dressing 202 configured to be placed over a first wound 220, a second fluid flow path 210, a second wound dressing 204 configured to be placed over a second wound 222, an inlet manifold branching attachment 206, and a third fluid flow path 212. The TNP apparatus 102 can be used to treat the first wound 220 using the first wound dressing 202 that is in fluidic communication with the TNP apparatus 102 via the first fluid flow path 208, the inlet manifold branching attachment 206, and the third fluid flow path 212. The TNP apparatus 102 can also be used to treat the second wound 222 using the second wound dressing 204 that is in fluidic communication with the TNP apparatus 102 via the second fluid flow path 210, the inlet manifold branching attachment 206, and the third fluid flow path 212.

Figure 12A:
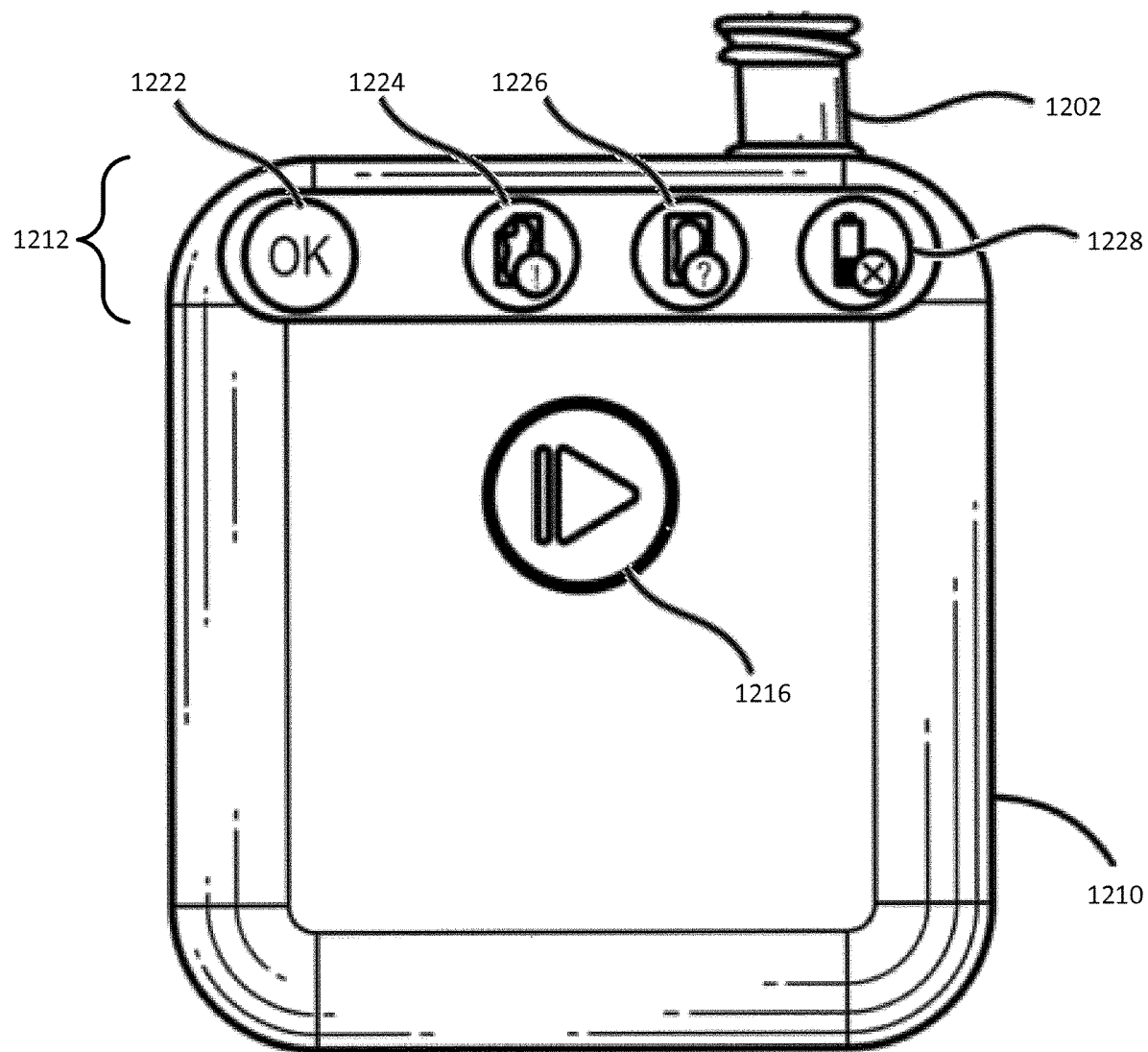
FIGS. 12A-12C illustrate portable negative pressure apparatuses according to some embodiments.
Figure 12B:
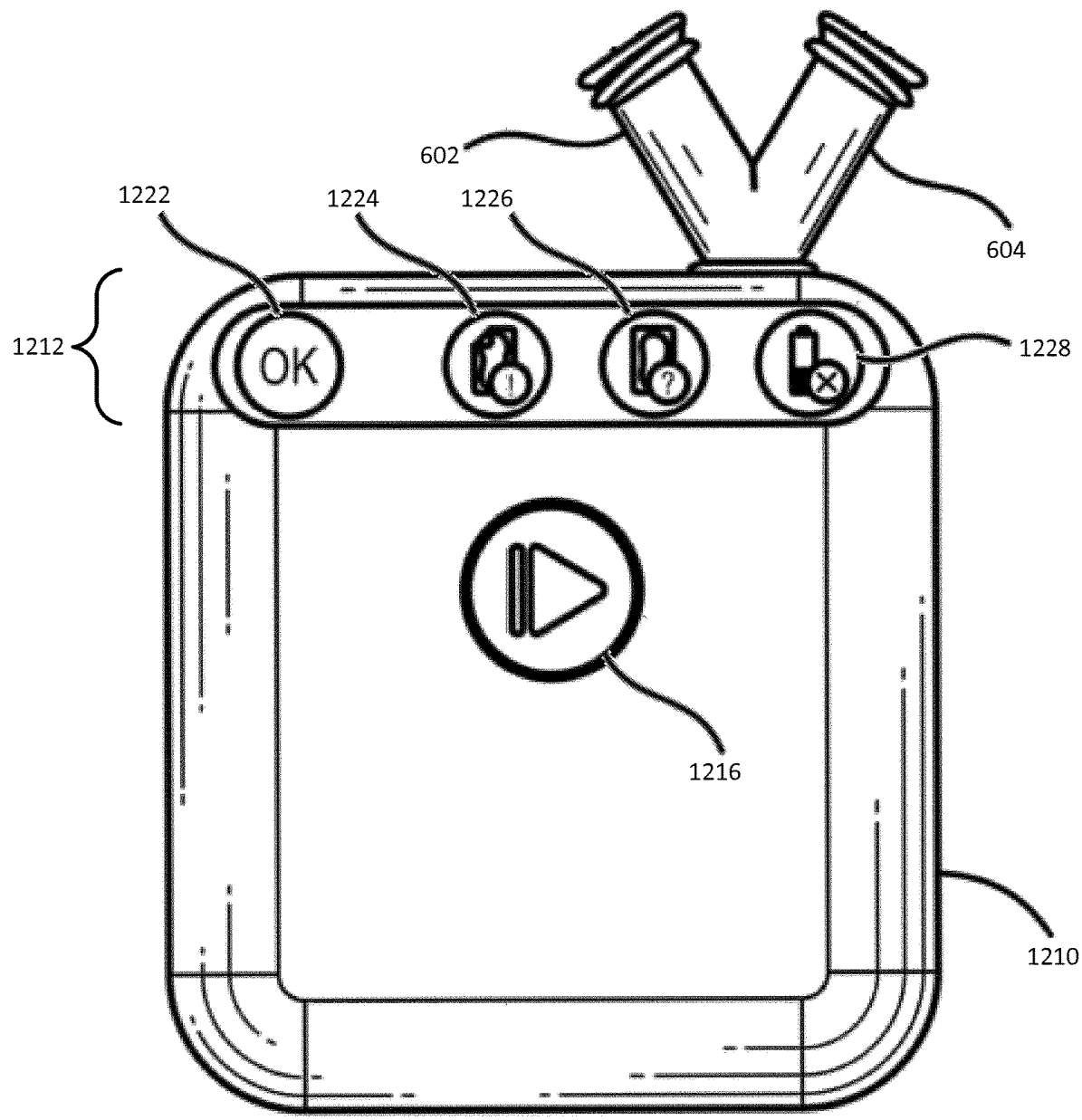
Figure 12C:
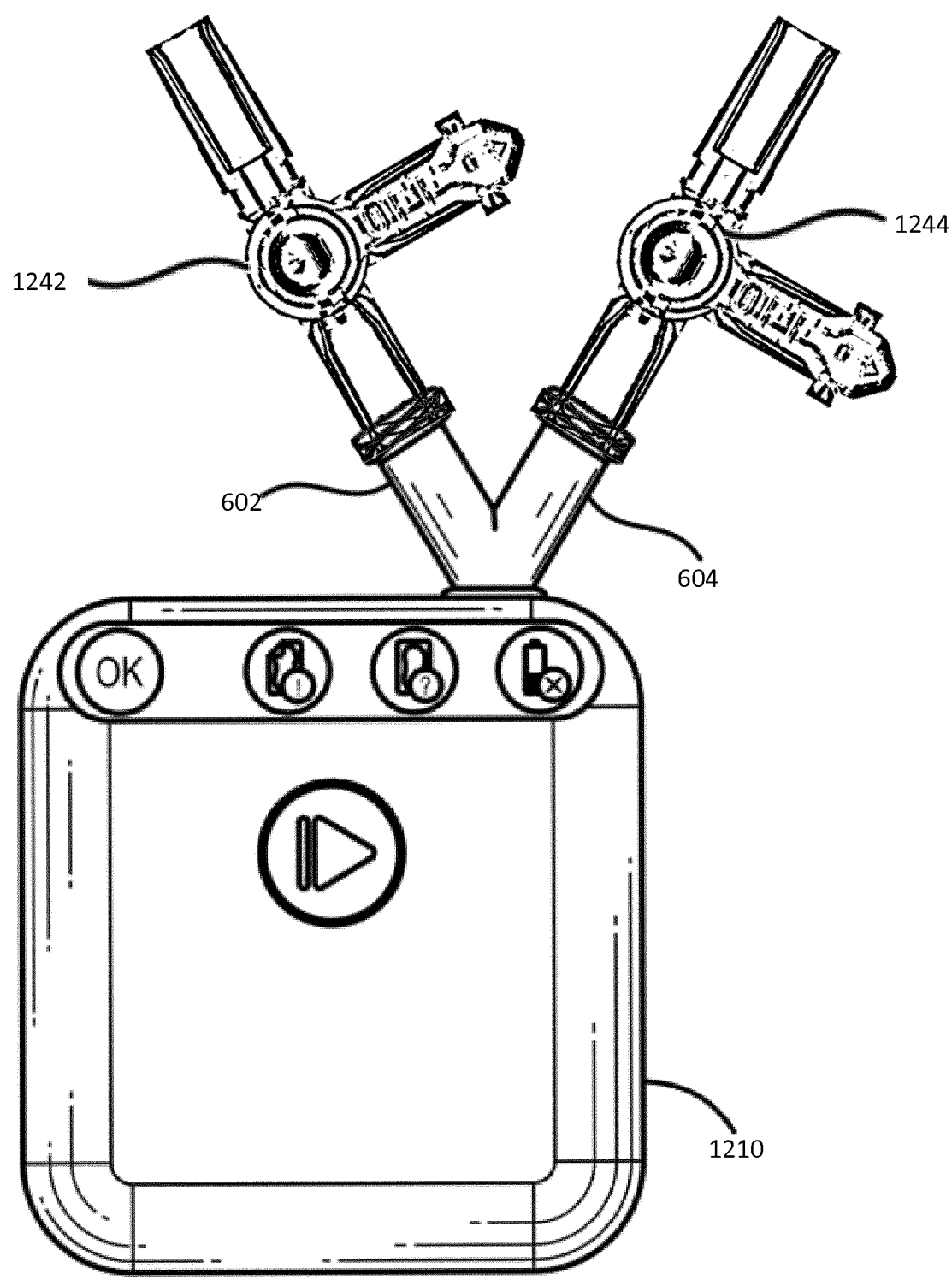
Figure 12D:
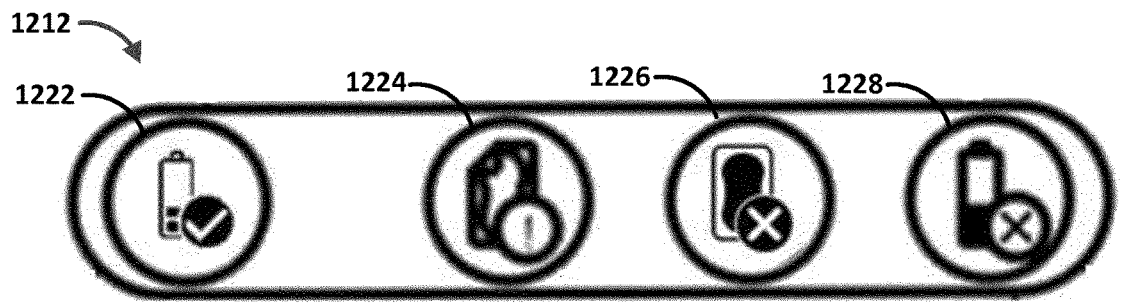
FIGS. 12D-12G illustrate user interfaces for a portable negative pressure apparatus according to some embodiments.
Figure 12E:
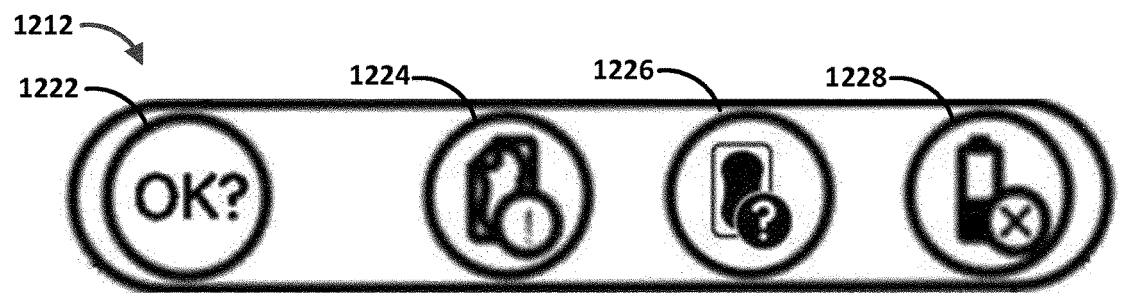
Figure 12F:
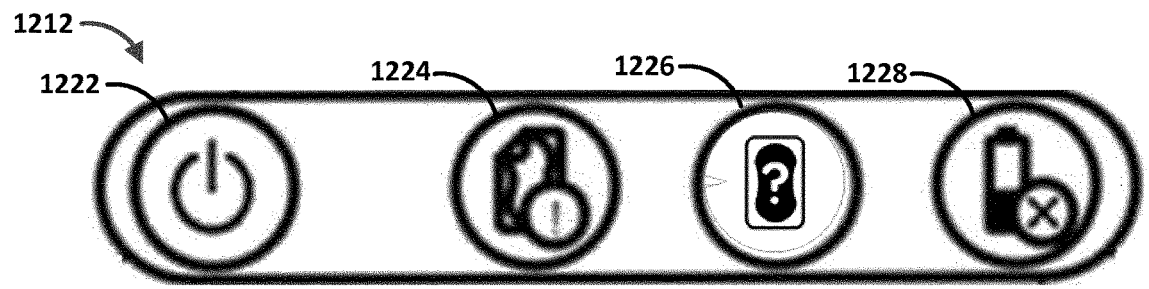
Figure 12G:
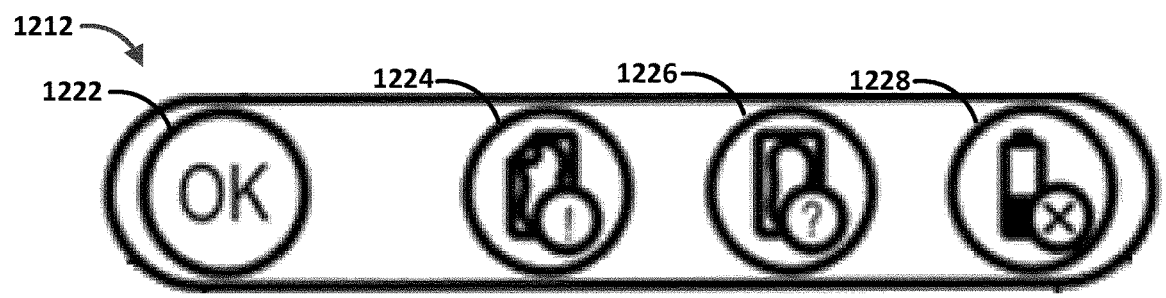

The inlet manifold branching attachment 206 is attached between the TNP apparatus 102 and the first and second wound dressings, thereby advantageously enabling the TNP apparatus 102 to generate and maintain negative pressure in or under both of the wound dressings simultaneously. In this example, the inlet manifolds are not incorporated into the TNP apparatus. Instead, an inlet manifold branching attachment 206, such as a Y-shaped connector, is used to connect the first and second fluid flow paths 208-B to the third fluid flow path 212. In other examples, inlet manifolds can be incorporated into the TNP apparatus 102 (as shown in FIGS. 12A-12C) such that the first and second fluid flow paths connect directly to the TNP apparatus via integrated inlet manifolds.

A pressure sensor 114 is positioned in the third fluid flow path 212, such as at or near an inlet of the TNP apparatus 102, to measure pressure in the third fluid flow path 212. The controller of the TNP apparatus 102 can monitor the pressure measured by the pressure sensor 114 and determine whether an operating condition (for example, a blockage, leakage, overpressure, or dressing full condition) has occurred in within the negative pressure therapy system 200.

In some instances, the controller can determine that an operating condition exists by comparing the measured pressure to an expected measured pressure (or flow). An "expected" pressure (or flow) can be the pressure measured by a pressure sensor in a negative pressure system operating in a normal state. The expected pressure can be equivalent or almost equivalent (for example, within 1, 2, 3, 4, 5, 10, 15, or 20 mmHg) to a pressure supplied by the negative pressure source (or a pressure selected by a user). In contrast, an "unexpected" pressure (or flow) can be any measured pressure other than the expected pressure (or flow). For instance, in some examples, a wound dressing experiencing a blockage, overpressure, or dressing full condition, can cause the pressure sensor to measure a lower (for example, more positive pressure) than expected pressure. In other examples, a wound dressing experiencing a leakage condition can cause the pressure sensor to measure a lower than expected pressure. In some examples, an operating condition can change the measured pressure (for example, spike, dip, increase, or decrease in measured pressure). In some embodiments, measured pressure is compared to one or more thresholds in order to determine if it is expected or unexpected.

In some examples, the TNP apparatus 102 will only function (for example, provide negative pressure) when two or more wound dressings are connected. Additionally, some indicators or functionality of the TNP apparatus that is available when only a single wound dressing is connected may be disabled so as not to confuse the user. For example, in some instances the dressing full indicator is not available for TNP systems having more than one connected wound dressing. Thus, the dressing full indicator(s) can be disabled or removed from the front panel so as not to confuse the user with unavailable functionality.

Figure 3:
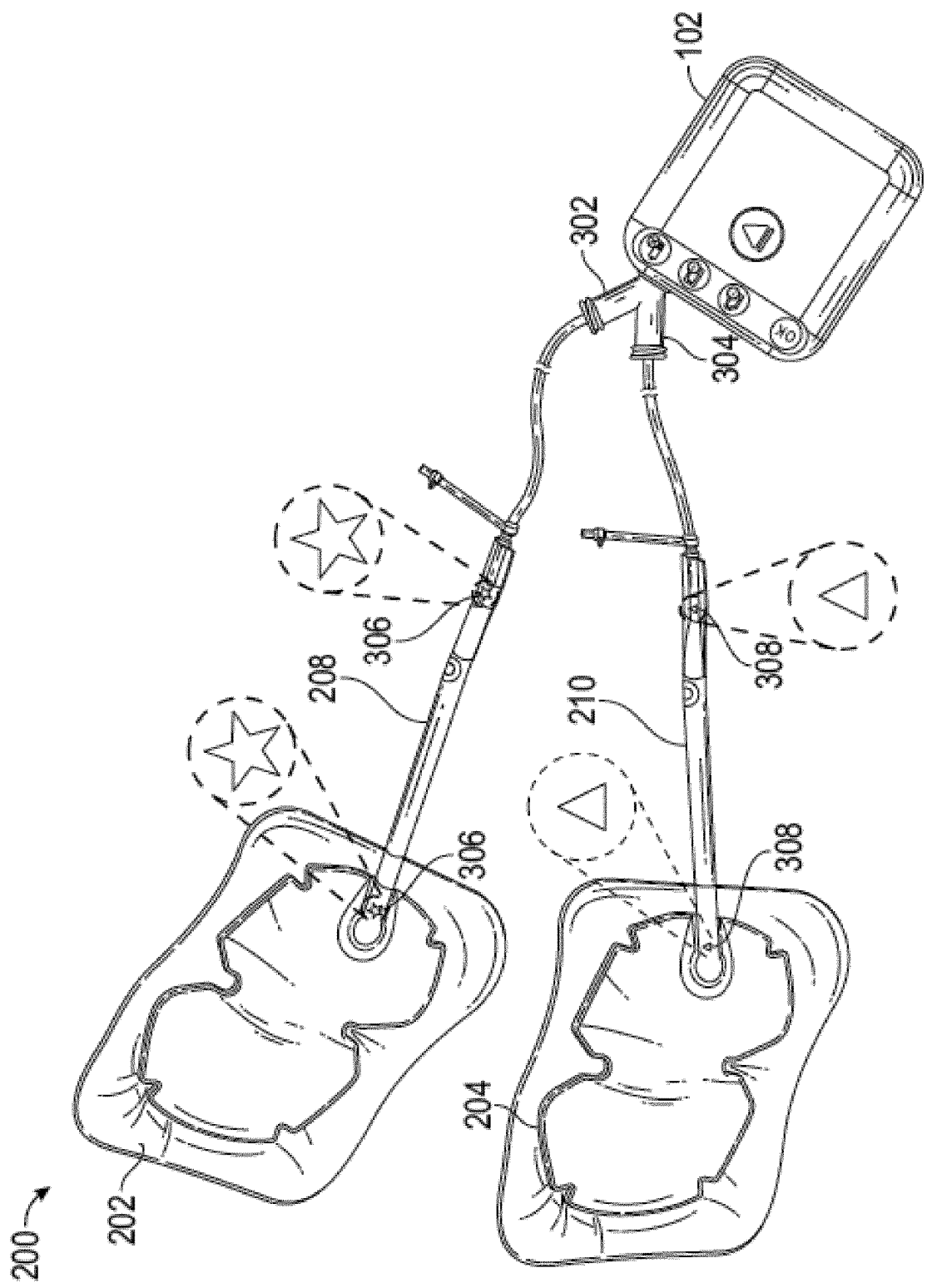
FIG. 3 illustrates some embodiments of negative pressure therapy system 200 of FIG. 2.

FIG. 3 illustrates some embodiments of negative pressure therapy system 200. The system 200 includes a TNP apparatus 102, a first fluid flow path 208, a first wound dressing 202, a second fluid flow path 210, a second wound dressing 204, a plurality of integrated inlet manifolds or connectors 302, 304. The plurality of integrated inlet manifolds 302, 304 are integrated with the TNP apparatus 102 and are fluidically connected to the first wound dressing 202 via the first fluid flow path 208 and the second wound dressing 204 via the second fluid flow path 210.

In some instances, a fluid flow path 208 can be lengthy and in a location remote from the TNP apparatus 102. As such, it can be desirable for the fluid flow paths to include one or more indicators 306, 308 which would be helpful to a user in identifying which fluid flow path 208 is connected to a particular inlet of the plurality of integrated inlet manifolds 306, 308.

As shown, the first fluid flow path 208 includes a plurality of first identifiers (stars) 306, and the second fluid flow path 208 includes a plurality of second identifiers (triangles) 308. In both instances, at least one identifier 306, 308 is located in close proximity to the inlet manifolds 306, 308 and at least one identifier is located in close proximity to a wound dressing. In some examples, a fluid flow path can include more than two identifiers 306, 308. For example, identifiers 306, 308 can be located across the length of the fluid flow path. Moreover, an identifier 306, 308 can alternatively include a printed glyph, a printed icon, an embossed glyph, an embossed icon, a braille character, a color-coding and the like. In some examples, an electronically controlled indication (such as an LED, an indicator on a display, etc.) is associated with each fluid flow path. This facilitates the TNP apparatus 102 in indicating an operating condition that may have occurred on the associated dressing.

In some embodiments, at least one pressure sensor can be positioned with an inlet manifold (either an integrated manifold or attachment manifold) to measure the combined pressure of the first and second fluid flow paths. The controller of the TNP apparatus 102 monitors the pressure measured by the pressure sensor and determines whether an operating condition has occurred in any of the fluid flow paths. In some aspects, the controller can be configured to provide a first indication associated with an operating condition in the first fluid flow path 208 and a second indication associated with an operating condition in the second fluid flow path 210.

In some examples, a negative pressure therapy system includes more than two wound dressings. Accordingly, the number of fluids flow paths and inlets can correspond with the number of wound dressings. For instance, a negative pressure therapy system having four wound dressings can have at least four fluid flow paths and at least four inlets manifolds. In some examples, a single wound dressing can be configured to communicate with a TNP apparatus via more than one fluid flow path. In some examples, the negative pressure therapy system can include more inlets manifolds than fluid flow paths and/or wound dressings. In examples such as these, the additional inlets can be disregarded or plugged.

Figure 4A:
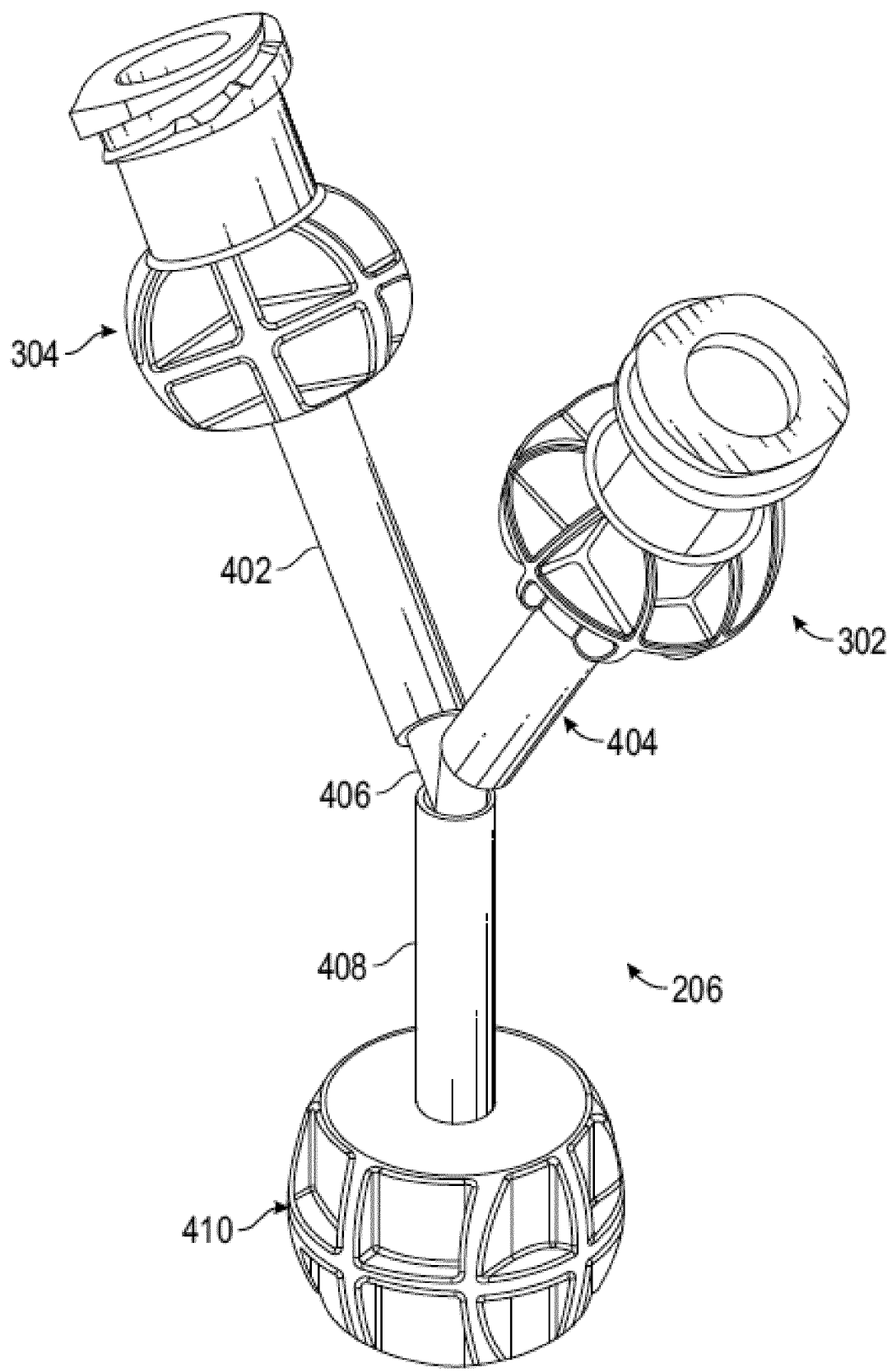
FIGS. 4A-C illustrate the inlet manifold branching attachment of FIG. 3 according to some embodiments.
Figure 4B:
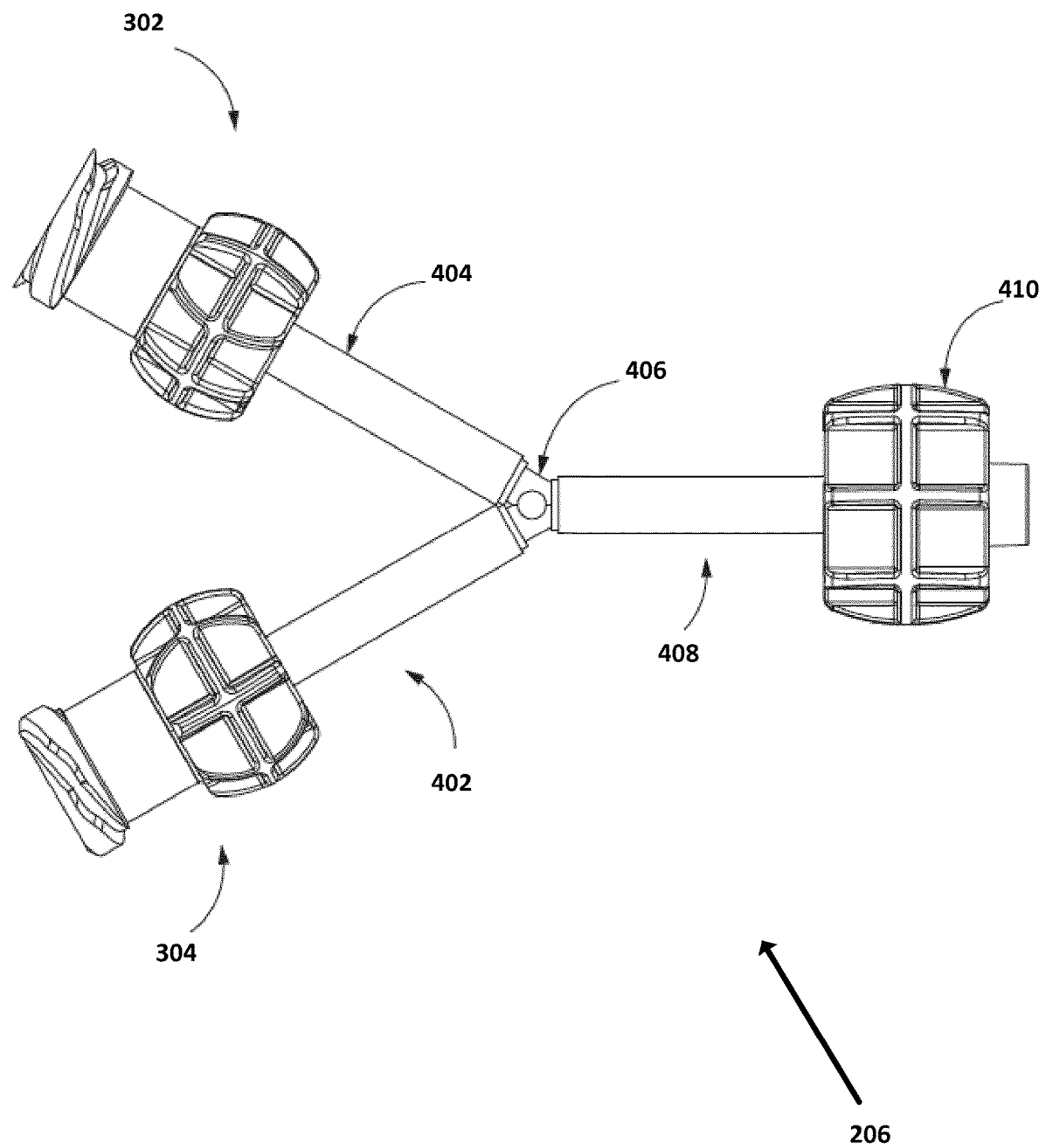
Figure 4C:
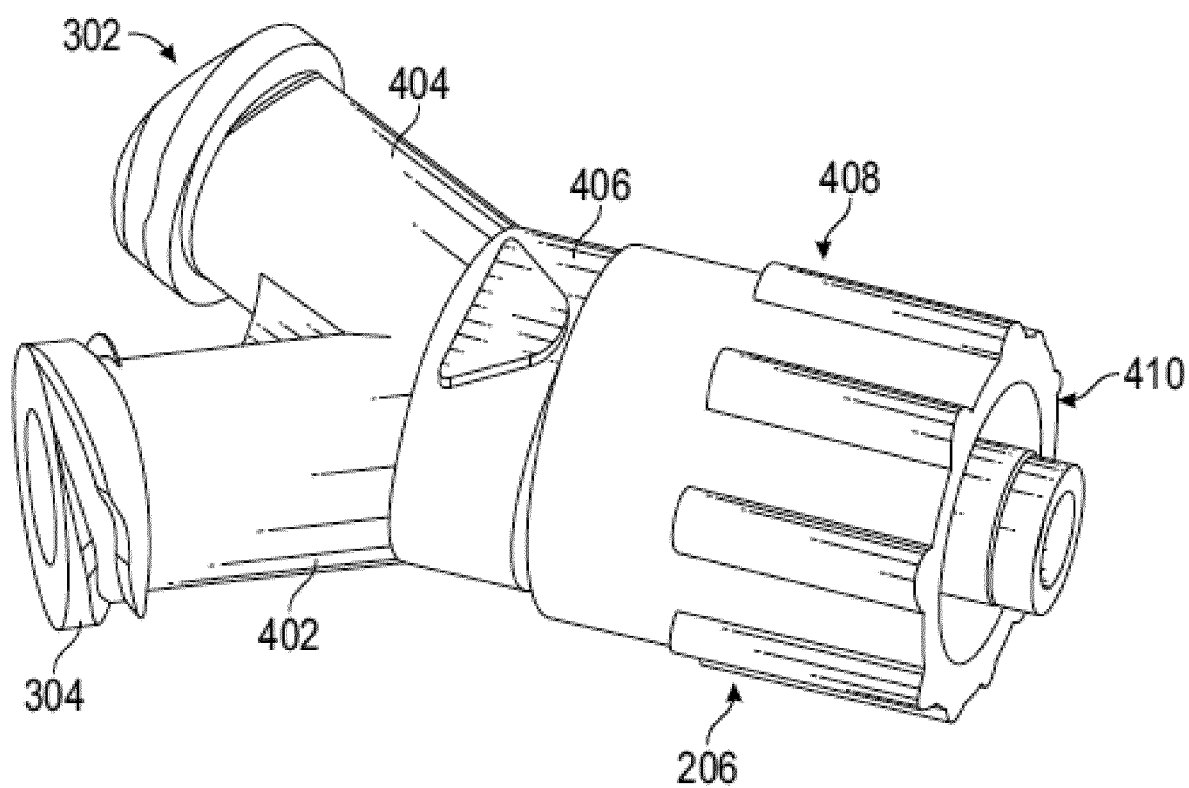

FIGS. 4A-4C illustrate an inlet manifold branching attachment 206 according to some embodiments. In some examples, the inlet manifold branching attachment 206 can be used in place of the integrated inlet manifold of FIG. 3. As illustrated, the Y-shaped inlet manifold branching attachment 206 can include three conduit attachment portions 306, 308, 410. A pump conduit attachment portion 410 can be used to connect to a conduit or tubing extending from a pump or TNP apparatus or to connect to the pump itself. The pump conduit attachment portion 410 can include a male non-luer connector at a proximal end of the Y-shaped inlet manifold branching attachment. The male connector can attach to a female connector of a conduit or pump. The pump conduit attachment portion 410 has a shaft 408 extending from the attachment portion and forming the bottom portion of the Y shape of the inlet manifold branching attachment 206.

The Y-shaped inlet manifold branching attachment also includes two dressing conduit attachment portions 306, 308. The dressing conduit attachment portions 306, 308 can be used to connect to the coupling of the fluid flow path extending from a wound dressing. In some embodiments, a conduit or tubing can be used to connect the inlet manifold branching attachment to the Y-shaped inlet manifold branching attachment 206. The conduit or tubing may be a soft bridge, a hard tube, or any other apparatus that may serve to transport fluid. The conduit or tubing can include a coupling at a proximal end and at a distal end. The conduit or tubing can be connected to the coupling of the inlet manifold branching attachment at the distal end and connected to the conduit attachment portions of the Y-shaped inlet manifold branching attachment at the proximal end of the conduit.

The dressing conduit attachment portion 306, 308 can include a female non-luer connector at a distal end of the Y-shaped inlet manifold branching attachment. The female connector can attach to a male connector of the coupling of the inlet manifold branching attachment or to the coupling of the conduit.

In some embodiments, the inlet manifold branching attachment 206 or the conduit can include incorporated valve(s), clamp(s), cap(s), and/or other closure mechanisms. Accordingly, flow or passage of fluid to and from one wound dressing can be blocked while another wound dressing continues to apply negative pressure. In some embodiments, the closure mechanism can be a valve, for example, a non-return valve.

In some examples, the valves incorporated in the Y-shaped inlet manifold branching attachment 206 are manual shut-off valves. For instance, a user can manually close a valve associated with conduit attachment portion 306 thereby blocking the fluid flow to and from the first wound dressing 202. Similarly, a user can manually close a valve associated with conduit attachment portion 308 thereby blocking the fluid flow to and from the second wound dressing 204. In some examples, a valve exists in conduit attachment potion 410, wherein closure of said valve would block fluid flow to and from the first and second wound dressings 202, 204.

In some examples, the valves incorporated in the Y-shaped inlet manifold branching attachment 206 are electromechanical valves. For instance, a controller (for example, the controller of the TNP apparatus as described in FIG. 1) can communicate with the valves to open and/or close each valve individually or as a unit. The communication between the valves and the TNP apparatus 102 can be wired or wireless. For instance, a wireless transceiver (e.g., see FIG. 1) of TNP apparatus 102 can communicate with a wireless transceiver of the valves. The wireless transceiver of the valves can be positioned within the inlet manifold branching attachment 206 or within close proximity to the inlet manifold branching attachment 206.

The dressing conduit attachment portions 306, 308 include shafts 404, 402, respectively, forming the top portions of the Y shape of the connector. The proximal ends of shafts 404, 402 and the distal end of shaft 408 meet at a joint 406. In some embodiments, the joint 406 can include a hinge that allows rotation of the shafts 404, 402, 408 about the joint 406. In some embodiments, only shafts 404, 402 of the dressing conduit attachment portions can move relative to the joint 406 and the shaft 408 of the pump conduit attachment portion is fixed. In some embodiments, the whole Y-shaped inlet manifold branching attachment will be in two parts that allow 360° rotation. FIG. 4C illustrates an embodiment of the Y-shaped inlet manifold branching attachment that is formed of two freely rotating parts that allow rotation of each part relative to the other. The rotation of the Y-shaped inlet manifold branching attachment can allow the user to twist the pump around while the wound dressings and conduits extending from the wound dressings remain stationary.

In some embodiments, the male and female non-luer connectors can be a rigid plastic. In some embodiments, the shafts 408, 404, 402 can be a flexible plastic tubing. In some embodiments, the Y-shaped inlet manifold branching attachment can be encased in a soft silicone sleeve to increase patient comfort and prevent the Y-shaped inlet manifold branching attachment from becoming a pressure point.

Utilizing the Y-shaped inlet manifold branching attachment 206 illustrated in FIGS. 4A-4C to attach a single pump to the two wound dressings, the TNP apparatus 102 can draw pressure in the two wound dressings simultaneously. The performance and fluid management of the multisite dressing and Y-connector is equivalent to a control test of the standard single wound dressing with single pump set-up. Although the attachment 206 is illustrated as being Y-shaped, the attachment 206 can be of any suitable shape or combination of shapes in some implementations. In some embodiments, luer, quick release, or other types of connectors can be used as one or more connectors of the attachment 206, the TNP apparatus 102, and one or more of the fluid flow paths 208, 210.

In some examples, a negative pressure therapy system can include more than two wound dressings and associated fluid flow paths in fluidic communication with the inlet manifold branching attachment. As such, in some embodiments, the inlet manifold branching attachment is attached to more than one TNP apparatus and/or more than two fluid flow paths (such as, one pressure source and three wound dressings ("1:3"), 1:4, 1:5, 2:1, 2:2, 2:3, 2:4, 2:5). The inlet manifold branching attachment can be a separate attachment, such as the Y-shaped connector that can connect to the third fluid flow path, or inlet manifolds can be incorporated into the TNP apparatus 102. The total number of inlet manifolds (for example, the number of "splits" performed by the inlet manifold branching attachment) that the inlet manifold branching attachment contains can be the same as the number of dressings to be connected. In some instances, one or more inlet manifolds connect to a single wound dressing.

Figure 5:
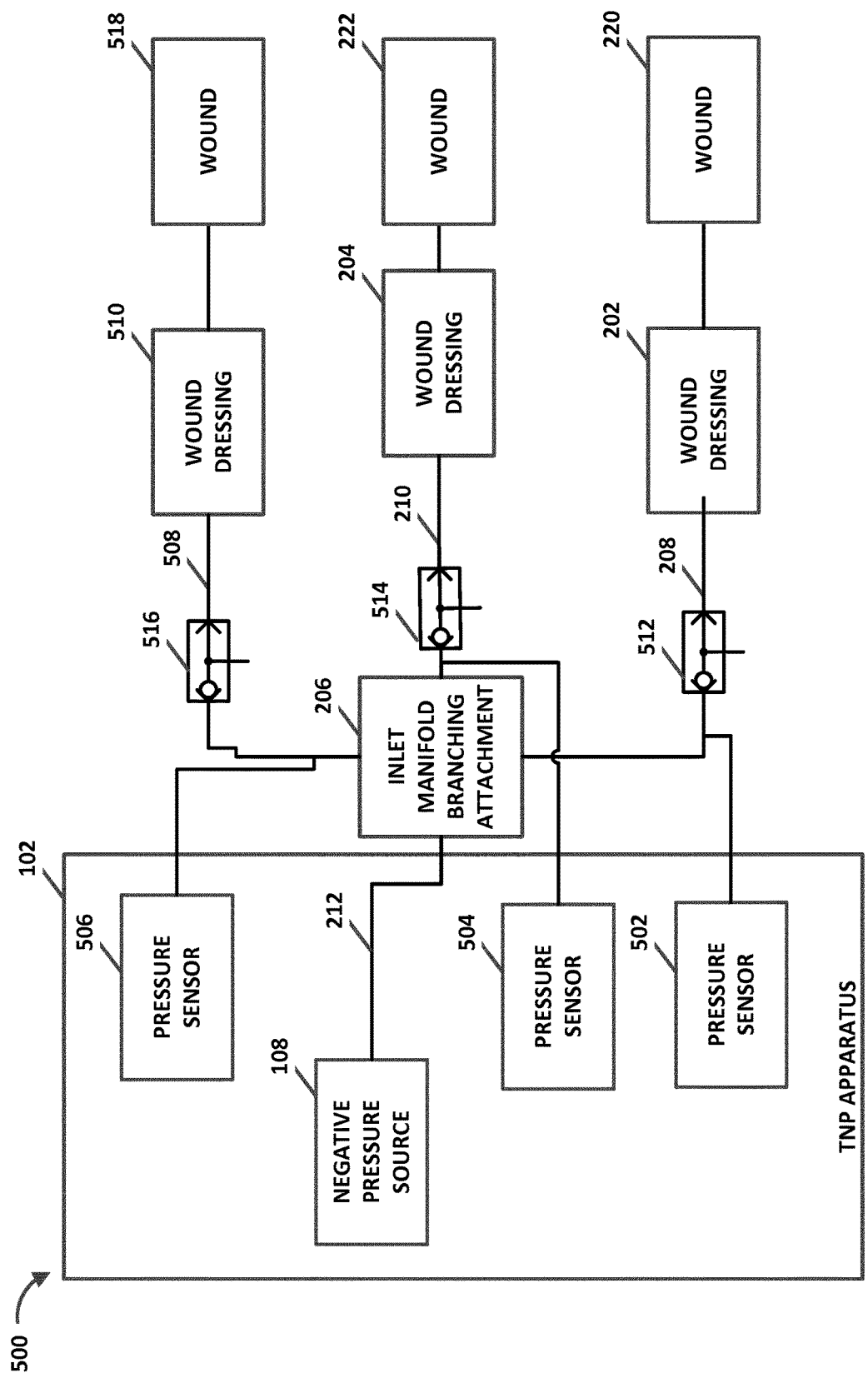
FIG. 5 illustrates a diagram of a negative pressure wound treatment system according to some embodiments.

FIG. 5 illustrates a negative pressure therapy system 500 having pressure sensors 502, 504, 506 positioned to measure each fluid flow path associated with wound dressings. In particular, a first pressure sensor 502 measure pressures in a first fluid flow path 208; a second pressure sensor 504 measured the pressure in a second fluid flow path 210; and a third pressure sensor 506 measures the pressure in a third fluid flow path 212.

By positioning a sensor within each of the fluid flow paths, the controller can monitor the pressure of each fluid flow path to determine whether an operating condition has occurred in the negative pressure therapy system 500. Additionally, because a sensor measures pressure on each of the fluid flow paths, upon determination of an operating condition, the controller can specifically determine which flow path/wound dressing combination is experiencing an operating condition. The negative pressure therapy system 500 provides the capability to monitor the functionality of individual wound dressings, thereby enabling the same set of features and functionality offered by a negative pressure therapy system utilizing a single wound dressing.

The pressure sensors 502, 504, 506 can be positioned anywhere in the fluid flow paths, such as between the wound dressings and the inlet manifold branching attachment 206 or at or near a wound dressing. In some examples, to reduce costs, the number of pressure sensors is one fewer than the number of wound dressings. For instance, where the number of wound dressings is N, only N−1 pressure sensors are employed in the negative pressure therapy system. In examples such as these, a controller can perform a process to determine whether the dressing without an associated pressure sensor is experiencing an operating condition. In some examples, as described above with respect to FIGS. 4A-C, one or more pressure sensors into an inlet manifold branching attachment 206.

A plurality of shut-off valves 512, 514, 516 (for example, as illustrated in FIG. 12C) can be positioned in the negative pressure therapy system 500 such that the closure of a valve blocks passage of fluid to and from an associated wound dressing. The shut-off valves 512, 514, 516 can be positioned anywhere in the fluid flow path, such as between the inlet manifold branching attachment 206 outlet and a corresponding dressing inlet. In some examples, as described above with respect to FIGS. 4A-C, one or more shut-off valves are integrated into an inlet manifold branching attachment 206.

In some examples, the valves 512, 514, 516 are manual shut-off valves. For instance, a user can manually close the first valve 512 thereby blocking the fluid flow to and from the first wound dressing 202. In other examples, the valves are electromechanical valves. For instance, the TNP apparatus 102 can communicate with the valves to open and/or close each valve individually or as a unit. The communication between the valves and the TNP apparatus 102 can be wired or wireless. For instance, a wireless transceiver (see e.g., FIG. 1) of TNP apparatus 102 can communicate with a wireless transceiver of the valves. In some cases, the wireless transceiver of the valves can be positioned within the inlet manifold branching attachment 206 or within close proximity to the inlet manifold branching attachment.

In TNP system 500, the controller can efficiently determine which fluid flow path/wound dressing combination is experiencing an operating condition and, in some embodiments, can close an associated valve to improve overall efficiency of the TNP apparatus. For instance, during normal operation in which no wound dressings are experiencing an operating condition, the pressure sensors 502, 504, 506 may measure approximately the same pressure. When a fluid flow path/wound dressing experiences an operating condition, the measured pressure associated with that fluid flow path/wound dressing changes such that a controller can determine: (1) which particular fluid flow path/wound dressing is experiencing the operating condition and/or (2) which particular type of operating condition is being experienced. For example, if pressure is measured downstream of a blockage that occurs in the first fluid flow path/wound dressing, the measured pressure in the first fluid flow path can increase (for example, become more negative) because the blockage restricts the fluid flow and consequently decreases the volume in which fluid flows. As another example, if pressure is measure upstream of the blockage in the first fluid flow path/wound dressing, the measured pressure in the first fluid flow path can decrease (for example, become more positive) because the blockage severely restricts or blocks fluid flow in part of the fluid flow path where pressure is measured. Due to this pressure change, the controller can determine that an operating condition (blockage) has occurred on the first fluid flow path/wound dressing. In some examples, operating conditions cause spike or spikes in measured pressure. In other examples, operating conditions cause an increase or decrease in measured pressure. The controller can make these determinations for blockage, overpressure, pressure leak, dressing full conditions, and the like.

In some examples, electronically controllable valves are utilized to shut-off therapy to specific dressings to prevent loss of pressure and improve overall efficiency of the TNP apparatus. This can be effective in a negative pressure therapy system having a large number of wound dressings.

Figure 6:
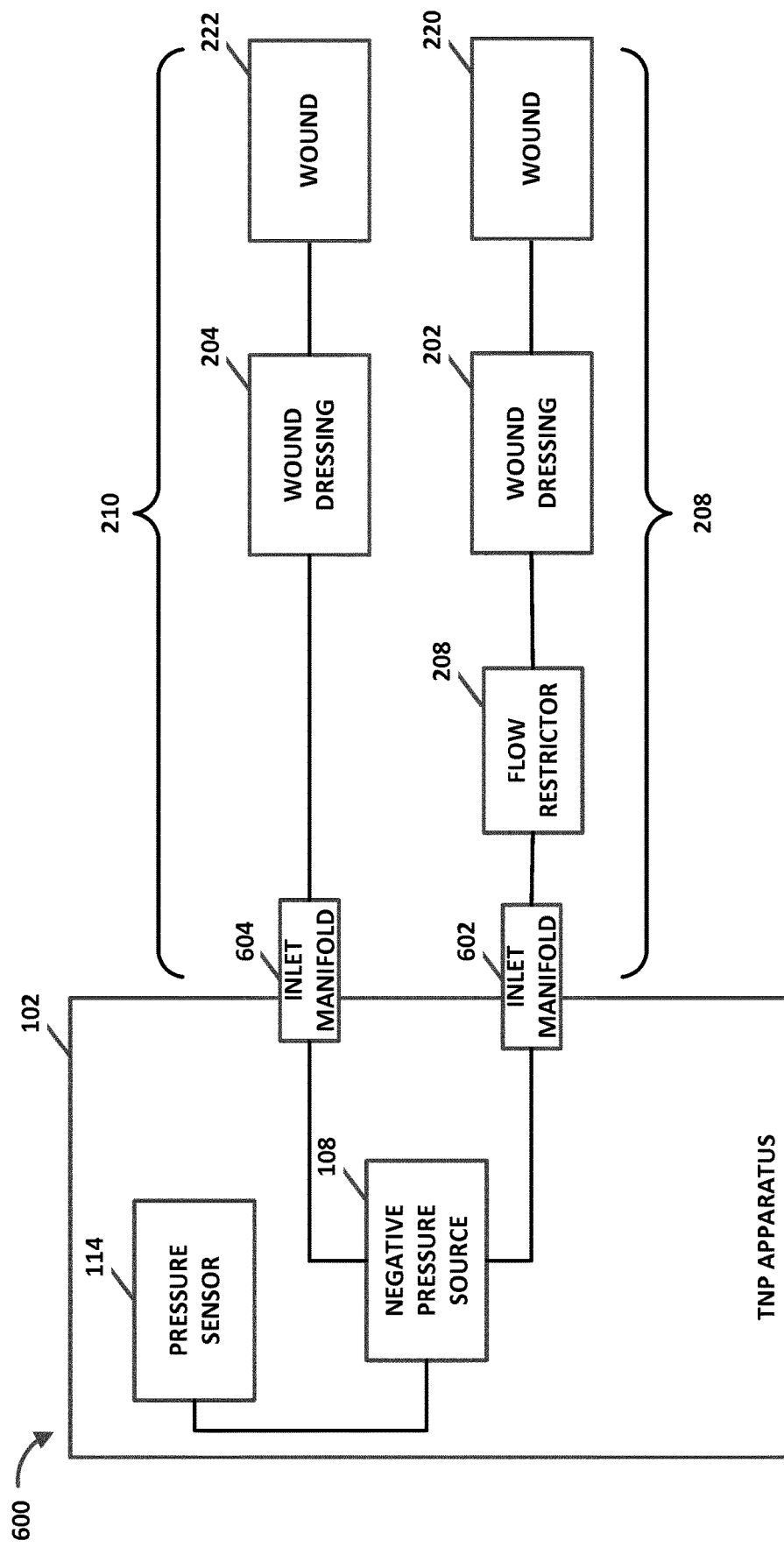
FIG. 6 illustrates a diagram of a negative pressure wound treatment system according to some embodiments.

FIG. 6 illustrates a negative pressure therapy system 600 according to some embodiments. The illustrated system differs from the negative pressure therapy system 200 in that it includes a flow reducer or restrictor 602 in the first fluid flow path 208 and a plurality of integrated inlet manifolds 602, 604 have replaced the inlet manifold branching attachment 206. In some implementations, the inlet manifolds 602, 604 can be replaced with a single inlet and a branching attachment 206 and the flow restrictor 602 can be integrated into one of the passageways or branches of the attachment 206. The addition of the flow restrictor 602 allows the controller to determine which wound dressing is experiencing an operating condition despite utilizing a single pressure sensor 114.

The flow restrictor 602 (such as a small volume receptacle or a small orifice) limits the flow through the first fluid flow 208 path such that the difference in flow between the first fluid flow path 208 and the second fluid flow path 210 can be perceived by the controller. For example, the TNP apparatus 102 can draw pressure in the two wound dressings simultaneously. The flow restrictor 602 restricts the pressure in the first fluid flow path 208. In some embodiments, during normal operation, flow detected by the system 600 (for example, a controller) will be the combination of flow through fluid flow paths 208 and 210, each of which may be known a priori (such as, calculated based on characteristics of each fluid flow paths, calculated via calibration, and the like). Upon the occurrence of an operating condition, such as blockage, in the first fluid flow path 208, detected flow will reduce to equal or nearly equal the flow through the flow path 210. Thus, the system 600 would not only detect change in flow, but would detect based on the measured flow that fluid is flowing through fluid flow path 210 and that fluid flow path 208 is experiencing a blockage. Similarly, the system 600 can detect and indicate an operating condition, such as a blockage, in fluid flow path 210. Indication of the operating condition can be performed using any of the approaches described herein, such as by audio-visual indication using an LED, display, and the like. For example, each of the fluid flow paths 208 and 210 may be associated with a particular color or symbol and such color or symbol can be displayed and/or announced. In some embodiments, measured flow is compared to one or more thresholds.

In some embodiments, flow (or flow rate) can be monitored or measured directly by using a flow meter. In some implementations, flow can be monitored or measured indirectly. For example, flow can be determined by monitoring the change in pressure measured by the pressure sensor 114. The controller can determine the rate of flow, for example, by determining a pressure gradient, rate of change of pressure, or pressure decay rate. As another example, in a system having a negative pressure source that produces variable flow, flow rate can be determined based on pressure and speed of the negative pressure source (such as pump motor). For example, flow rate can be determined according to Equation 1 below:

$$\text{Flow Rate} = C_1 * F * P + C_2 \qquad \text{(Equation 1)}$$

where F is the pump speed (such as, frequency of a tachometer signal that measures pump motor revolutions), P is measured pressure, and $C_1$ and $C_2$ are suitable constants. Additional details are described U.S. Pat. No. 8,905,985 and U.S. Patent Publication No. 2012/0001762, each of which is hereby incorporated by reference in its entirety.

In some embodiments, the flow restrictor 602 can be replaced with a flow enlarger configured to increase flow. In such cases, detection of an operating condition will be similar to the foregoing with the exception that the flow in the flow path 208 associated with the wound 220 is increased by the flow restrictor.

In some embodiments, the flow restrictor 602 is a permanent restrictor, such as an orifice with a smaller diameter than one or more of the conduits in the fluid flow path 208. In some implementations, the flow restrictor 602 is a temporary restrictor, such as an adjustable valve, that temporarily restricts the fluid flow when determination of whether an operating condition is present is made. In some examples, the controller can control the temporary flow restrictor. In certain embodiments, a plurality of flow reducers and/or enhancers could be utilized in a system that includes more than two wound dressings and associated fluid flow paths. For instance, a system with three wound dressings can include a flow restrictor in a first fluid flow path and a flow enhancer in a second fluid flow path. Similarly, a system with three wound dressings can include a flow restrictor in a first fluid flow path and a stronger (or more narrow) flow restrictor in a second fluid flow path. In any of these examples, the difference in flow rates among the plurality of fluid flow paths can permit the TNP apparatus to determine which fluid flow path/wound dressing is experiencing an operating condition.

In some examples, a canister can be coupled between the TNP apparatus 102 and/or the plurality of integrated inlet manifolds 602, 604. The canister can collect exudate removed from the wounds 220, 222. Alternatively, a canister can be coupled between each wound dressing and the inlet manifold branching attachment.

Figure 7:
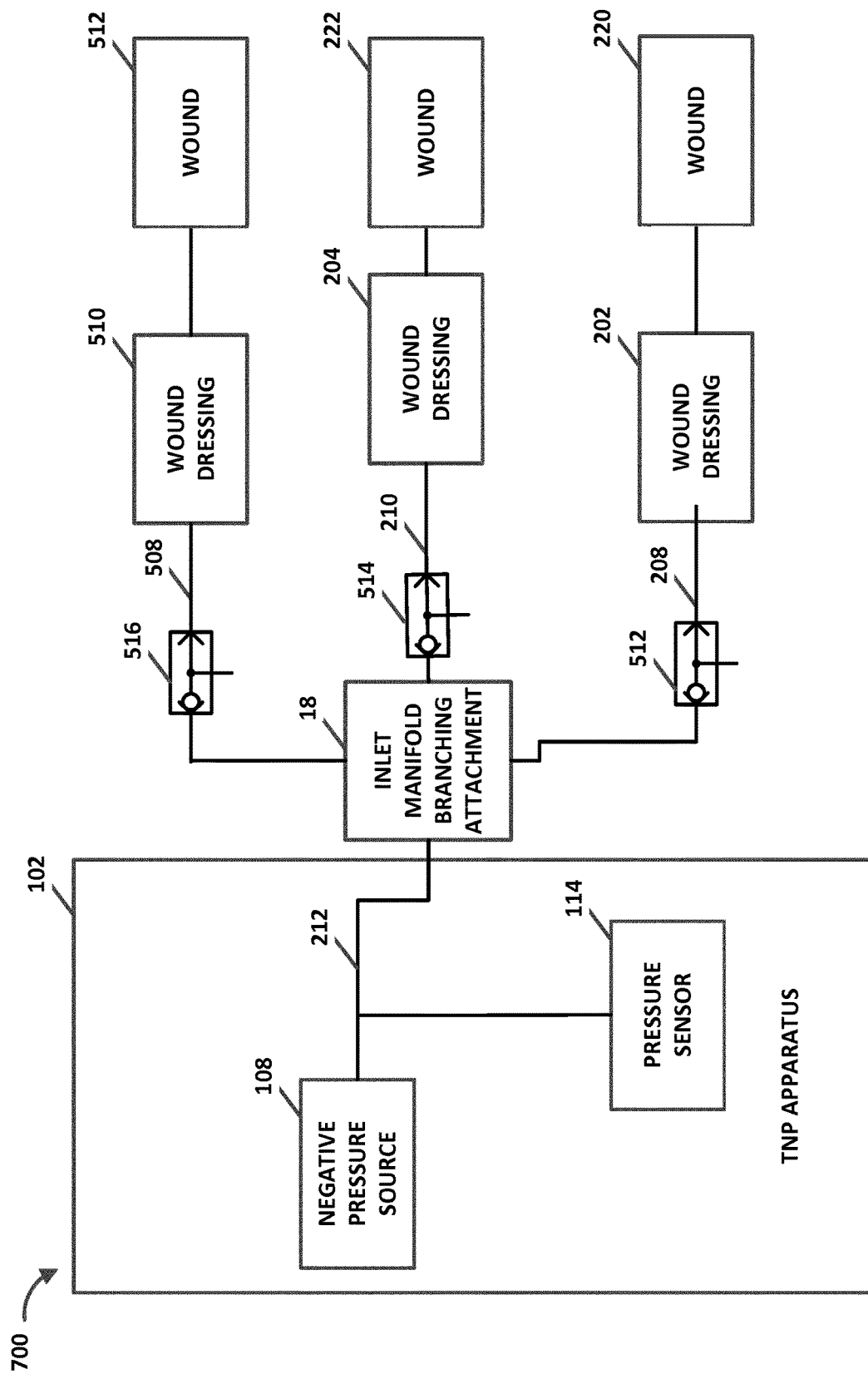
FIG. 7 illustrates a diagram of a negative pressure wound treatment system according to some embodiments.

FIG. 7 illustrates a negative pressure therapy system 700 according to some embodiments. System 700 differs from the negative pressure therapy system 200 in that system 700 includes a third wound dressing 510, a third wound 518, a fourth fluid flow path 508, and a plurality of shut-off valves 512, 514, 516. In addition to treating wounds 220-B as described in 200, the system 700 can be utilized to treat the third wound 518 using the third wound dressing 510 that is in fluidic communication with the TNP apparatus 102 via the fourth fluid flow path 508, the inlet manifold branching attachment 206, and the third fluid flow path 212.

The plurality of shut-off valves 512, 514, 516 are positioned in the fluid flow paths such that the closure of a corresponding valve blocks the fluid flow to and from the connected fluid flow path/dressing. The shut-off valve 21 can be positioned anywhere from the inlet manifold branching attachment 206 outlet to the corresponding dressing inlet. As illustrated, a first valve 512 is positioned on the first fluid flow path 208, a second valve 514 is positioned on the second fluid flow path 210 and a third valve 516 is positioned on the fourth fluid flow path 508.

In some examples, the plurality of valves 512, 514, 516 are manual shut-off valves. For instance, a user can manually close the first valve 512 thereby blocking the fluid flow to and from the first wound dressing 202. In other examples, each of the plurality of valves is an electromechanical valve. For instance, the TNP apparatus can communicate with the valves to open and/or close each valve individually or as a unit. The communication between the valves and the TNP apparatus 102 can be wired or wireless. For instance, a wireless transceiver (see e.g., FIG. 1) of TNP apparatus 102 can communicate with a wireless transceiver of the valves.

The wireless transceiver of the valves can be positioned within the inlet manifold branching attachment 206 or within close proximity to the inlet manifold branching attachment.

Figure 8A:
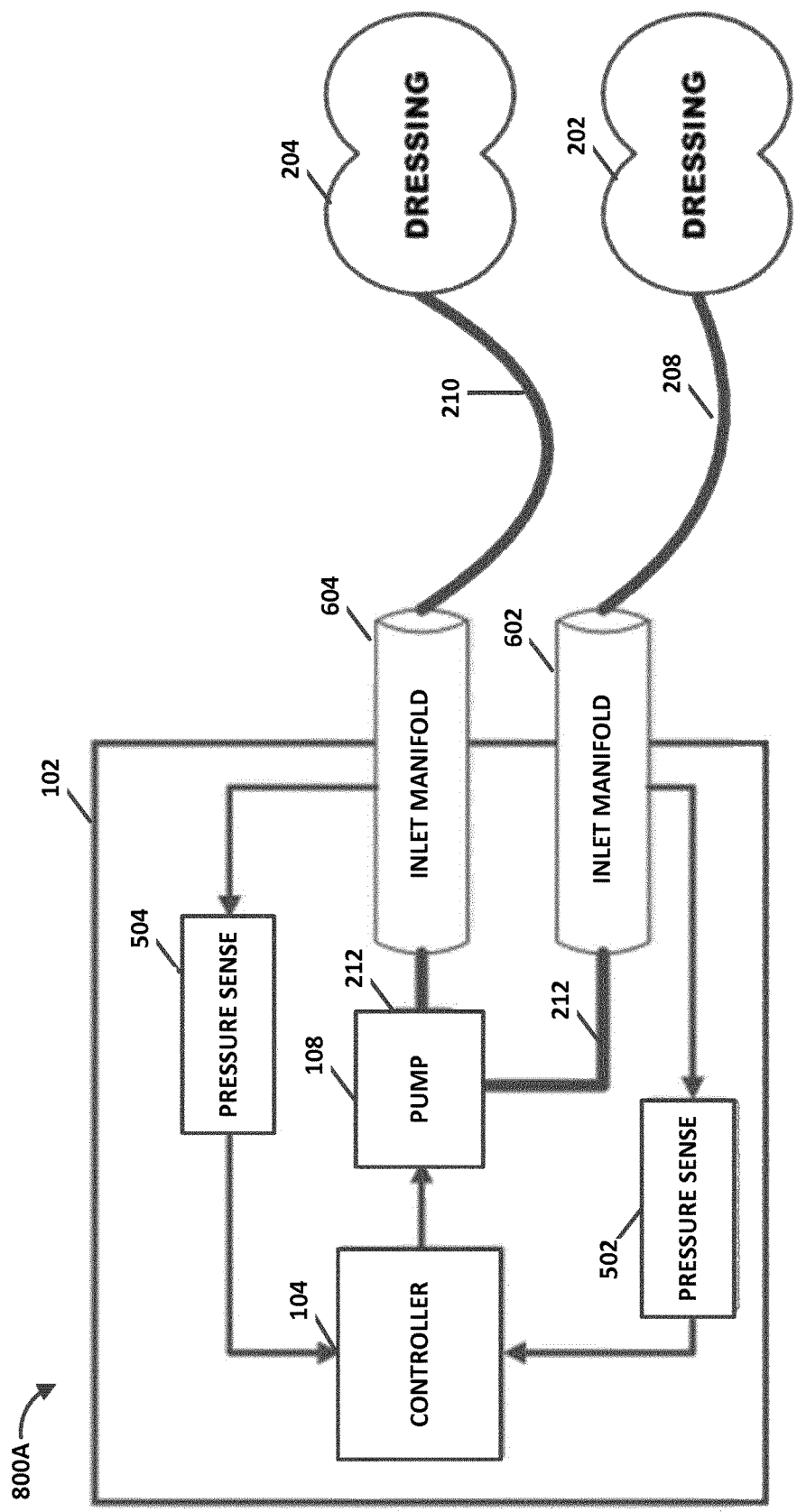
FIGS. 8A-8B illustrates diagrams of a TNP apparatus according to some embodiments.

FIG. 8A illustrate a negative pressure therapy system 800A according to some embodiments. In this example, the TNP apparatus 102 includes at least a controller 104, a negative pressure source 108, a plurality of pressure sensors 502, 504, and a plurality of integrated inlet manifolds 306, 308.

The integrated inlet manifolds 602, 604 can be combined into a single unit (e.g., as depicted in FIGS. 3 and 12), such that a single negative pressure passageway is connected to the negative pressure source 108. Alternatively, each of the plurality of integrated inlet manifolds 306, 308 can directly connect to the negative pressure source without first combining with another inlet manifold.

The plurality of pressure sensors 502, 504 are positioned such that a first pressure sensor 502 measures the pressure of the first fluid flow path 208 connected to the first inlet manifold 306 and a second pressure sensor 504 measures the pressure of the second fluid flow path 210 connected to the second inlet manifold 308. In some examples, the pressure sensors 502, 504 can be positioned within an inlet manifold. In other examples, the pressure sensors are located with a housing of the TNP apparatus 102.

Figure 8B:
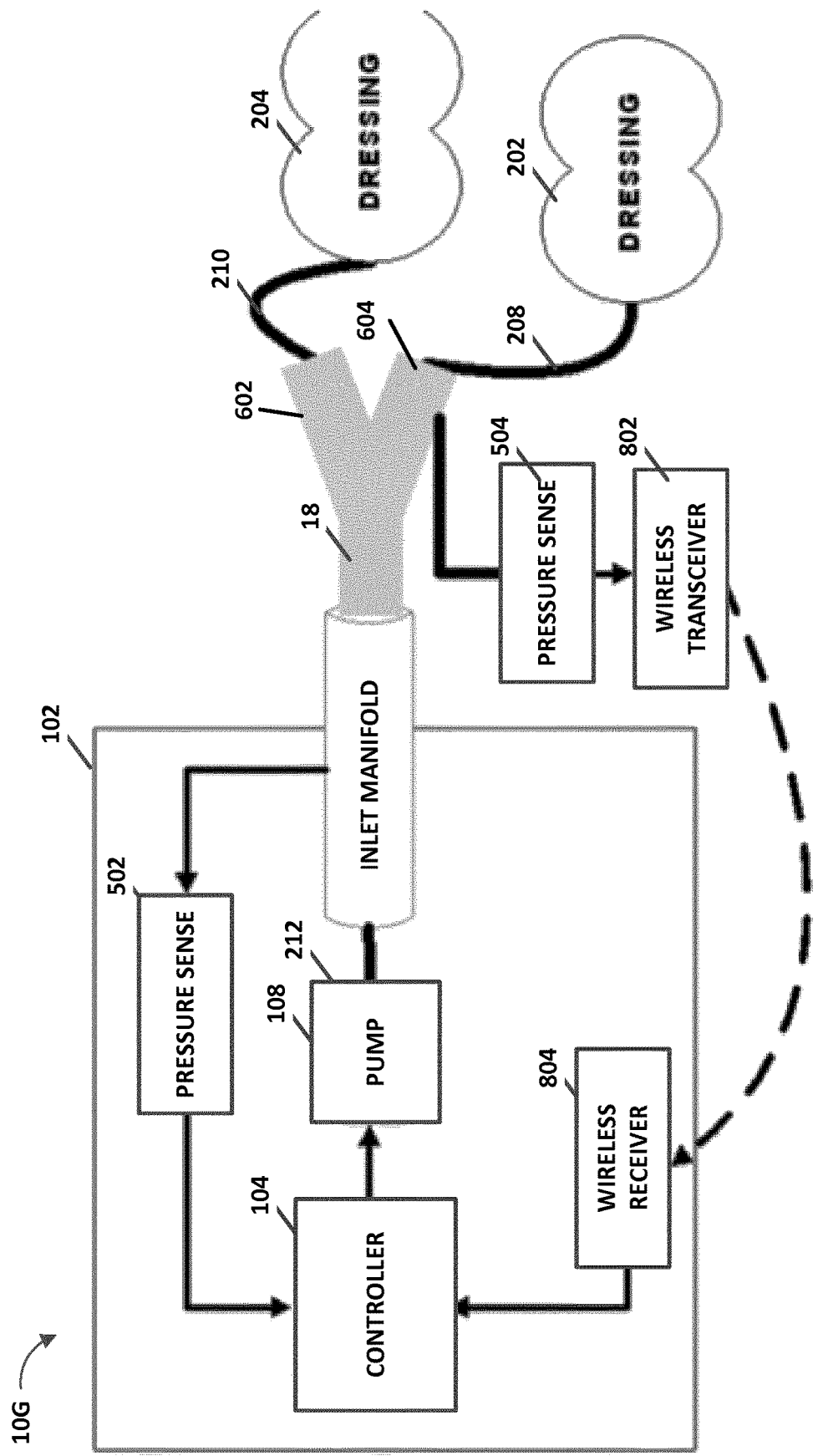

FIG. 8B illustrates a negative pressure therapy system 800B according to some embodiments. In this example, the system 800B includes an inlet manifold branching attachment 206. As described herein, inlet manifolds can include an inlet manifold branching attachment 206 (as illustrated in FIGS. 4A-4B) and/or can include one or more integrated inlet manifolds (as illustrated in FIGS. 12A-12C).

The inlet manifold branching attachment 206 includes a pressure sensor 504 on a first branch 308 fluidically connected to the first dressing 202 via the fluid flow path 208, as well as a wireless transceiver or receiver 802 to communicate with the wireless receiver 804 in communication with a controller 104 of the TNP apparatus 102. The pressure sensor 504 measures pressure in the fluid flow path 208, while pressure sensor 502 measures combined pressure in fluid flow paths 208 and 210. Operating conditions, such as blockages, in one or more of the fluid flow paths 208 or 210 can be determined based on pressure measured by the sensors 502 and 504 using any of the approaches described herein. In some examples, the inlet manifold branching attachment 206 can communicate with the TNP apparatus 102, for example, to provide pressure data. The communication can be wired or wireless (for example, over Bluetooth). In some examples, dressing-full detection and/or detection of other operating conditions can be used to provide indication(s) to the user.

Figure 9:
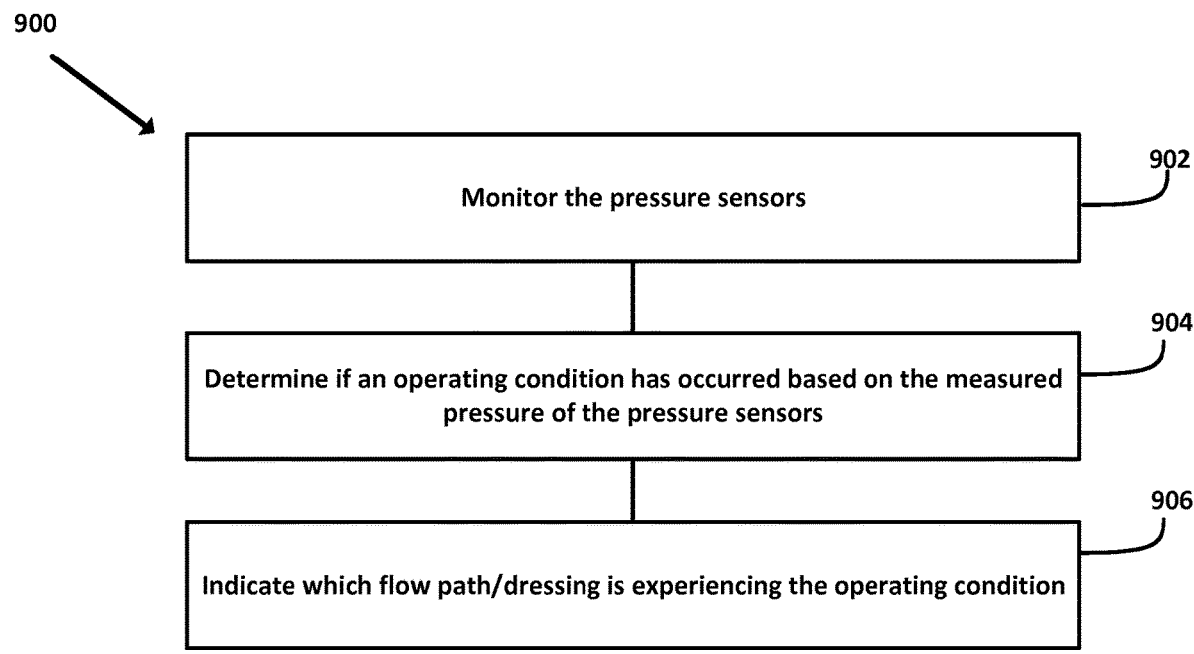
FIG. 9 illustrates a diagnostics process performed by a negative pressure wound treatment system according to some embodiments.

FIG. 9 illustrates a diagnostics process 900 performed by a negative pressure wound treatment system 500 (see e.g., FIG. 5) according to some embodiments. Process 900 can be performed by a controller of the negative pressure wound treatment system. As mentioned above, an operating condition can include a blockage, leakage, overpressure, dressing full condition, or the like. The process can detect one of the foregoing operating conditions by analysing the pressure measured by pressure sensors 502, 504, 506.

At block 902, the process monitors the pressure sensors 502, 504, 506 which measure pressure in various fluid flow paths 208, 210, and 508. In some examples, the controller monitors the pressure sensors 502, 504, 506 continuously, at predetermined intervals (such as, 1 minute, 2 minutes, 5 minutes, 10 minutes, 15 minutes, 20 minutes, 30 minutes, or 60 minutes), and/or responsive to input by a user.

At block 904, the process determines that an operating condition has occurred based at least in part on a change in pressure measured by one of the plurality of pressure sensors. For instance, an occurrence of a blockage in one of the wound dressings may cause a momentary or prolonged spike or dip in measured pressure. As another example, the process can determine flow based on measured pressure (or directly if one or more flowmeters are utilized). As described with respect to FIG. 5, by positioning a pressure sensor to monitor conditions in each of the fluid flow paths associated with the wound dressings, the process 900 can monitor the pressure sensors 502, 504, 506 and determine specifically which fluid flow path/wound dressing is experiencing an operating condition. Thus, the negative pressure therapy system 500 provides the capability to monitor the functionality of individual wound dressings, thereby enabling the same set of features offered by a negative pressure therapy system utilizing a single wound dressing.

At block 906, the process 900 provides indication of the flow path/dressing (or flow paths/dressings) determined to be experiencing an operating condition. In some examples, one or more LEDs or other indicators can be used to indicate to a user or caregiver that an operating condition has been detected. For example, each wound dressing can have a corresponding LED that is ON when no operating condition is detected on the associated wound dressing and OFF when an operating condition is detected on an associated wound dressing. In some examples, other indicators may be associated with wound dressing that is experiencing an operating condition, such as sounds, wireless messages, display notifications and/or other signals that may get the attention of a user or caregiver. In some examples, the TNP apparatus may additionally or alternatively provide indication by closing a valve associated with the wound dressing experiencing the operating condition.

Figure 10:
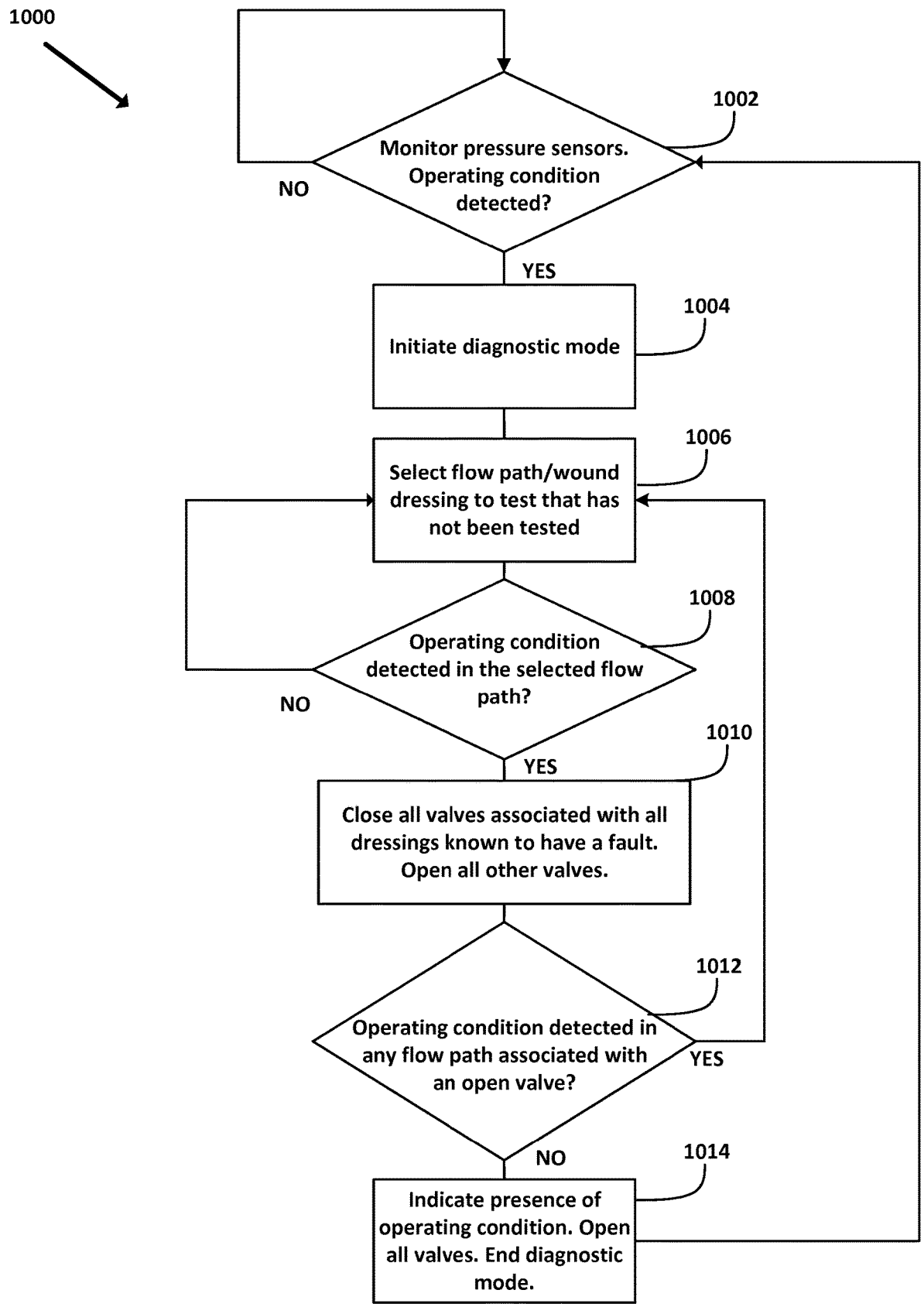
FIG. 10 illustrates a diagnostics process performed by a negative pressure wound treatment system according to some embodiments.

FIG. 10 illustrates a diagnostics process 1000 performed by a negative pressure wound treatment system 700 (see e.g., FIG. 7) according to some embodiments. Process 1000 can be performed by a controller of the negative pressure wound treatment system. As mentioned above, an operating condition can include a blockage, leakage, overpressure, dressing full condition, or the like. The process can detect one of the foregoing operating conditions by analysing the pressure measured by pressure sensor 502. When the process determines that an operating condition has occurred, it can initiate diagnostics to determine which flow path/dressing is experiencing an operating condition. In some examples, the process is implemented in firmware or software that incorporates a diagnostic mode to determine which flow path/wound dressing is experiencing an operating condition. In some examples, an operator can toggle between the operational modes through an interface of the TNP apparatus (such as, a touchscreen interface or dedicated buttons or switches).

At block 1002, the process 1000 monitors the pressure sensor 502, which measures pressure at or in the TNP apparatus 102. In some examples, the process 1000 continuously monitors the pressure sensor 502. In other examples, the process 1000 monitors the pressure sensor 502 at predetermined intervals (such as, 1 minute, 2 minutes, 5 minutes, 10 minutes, 15 minutes, 20 minutes, 30 minutes, or 60 minutes). In other examples, the process can monitor the pressure sensor responsive to input by a user.

At block 1004, the process determines that an operating condition has (or may have) occurred and initiates a diagnostic mode to determine which fluid flow path(s)/wound dressing(s) are experiencing an operating condition. During the diagnostic mode, the process can determine that an operating condition has occurred based at least in part on a change in pressure measured by the pressure sensor 502, change in flow, and the like. For instance, an occurrence of an operating condition on one of the fluid flow paths/wound dressings may cause a momentary or prolonged spike or dip in pressure measured by the pressure sensor 502.

In block 1006, a fluid flow path/wound dressing is selected for testing. In some examples, the user and/or the process can make this selection. For instance, the user can make the selection by providing input to the process. The section can be arbitrary, one based on the user's suspicions, or one based on the process's suggestion. In some examples, the process can make the selection. The process's selection, for instance, can be random, based on user input, or based on data within the controller.

The valve associated with the selected fluid flow path/dressing is opened and the valve(s) associated with the unselected dressing(s) are closed, thereby likening the negative therapy system to a negative pressure system having a single wound dressing fluidically connected to a negative pressure source. The valve(s) can be opened or closed manually by a user or by the controller. In some examples, the controller can electronically (such as, through a wired or wireless connection) control the shut-off valves. For instance, a wireless transmitter or transceiver of the TNP apparatus can communicate with a wireless transceiver or receiver of the valves. In such examples, the wireless transceiver can communicate with each of the valves and is capable of controlling each of the valves individually or as a unit.

At block 1008, the process monitors the pressure sensor 502 to determine if the selected dressing is experiencing an operating condition. This analysis may be similar to a determination made by a process in a negative pressure system having a single wound dressing fluidically connected to a negative pressure source. For example, a lower than expected negative pressure (or higher than expected flow) can indicate that a wound dressing is experiencing leakage and a higher than expected negative pressure (or lower than expected flow) can indicate that a wound dressing is experiencing a blockage, overpressure, or dressing full condition.

If the process determines that the selected wound dressing is not experiencing an operating condition (for example, the pressure measured by the pressure sensor 502 is generally equivalent to the expected pressure), then a different fluid flow path/wound dressing is selected for testing. That is, the process 1000 returns to block 1006). The newly selected fluid flow path/wound dressing will be a wound dressing that has not been tested during the current diagnostic mode.

At block 1010, the process determines that the previously selected wound dressing is experiencing an operating condition. The valve associated with the selected wound dressing is closed (along with closing any valves associated with a fluid flow paths(s)/wound dressing(s) previously determined to be experiencing an operating condition). All other valves are opened. As described above, the valves can be opened or closed manually by a user or automatically by the controller.

At block 1012, the process monitors the pressure sensor to determine if any of the fluid flow paths/wound dressings associated with open valves are experiencing an operating condition. For example, the pressure sensor may sense an expected pressure (or flow) if no operating conditions are present and may sense an unexpected pressure (or flow) if operating conditions are present. If the process determines that an operating condition is present among the wound dressing(s) associated with the open valve(s), then a new wound dressing is selected (block 1006). As described above, the newly selected wound dressing will be a wound dressing that has not been tested during the current diagnostic mode.

At block 1014, the process has determined which flow paths/wound dressings of the plurality of wound dressings are experiencing an operating condition. The process can provide appropriate indication as described herein, which facilitates addressing and remedying the operating condition. For example, if a dressing full operating condition is detected, wound dressings can be replaced. In some examples, the user must manually replace the wound dressings. In some examples, the wound dressings are replaced without the help of the user. At block 1014, all valves can be opened, and the diagnostic mode has been completed. As described above, the valves can be opened manually or electromechanically.

Figure 11:
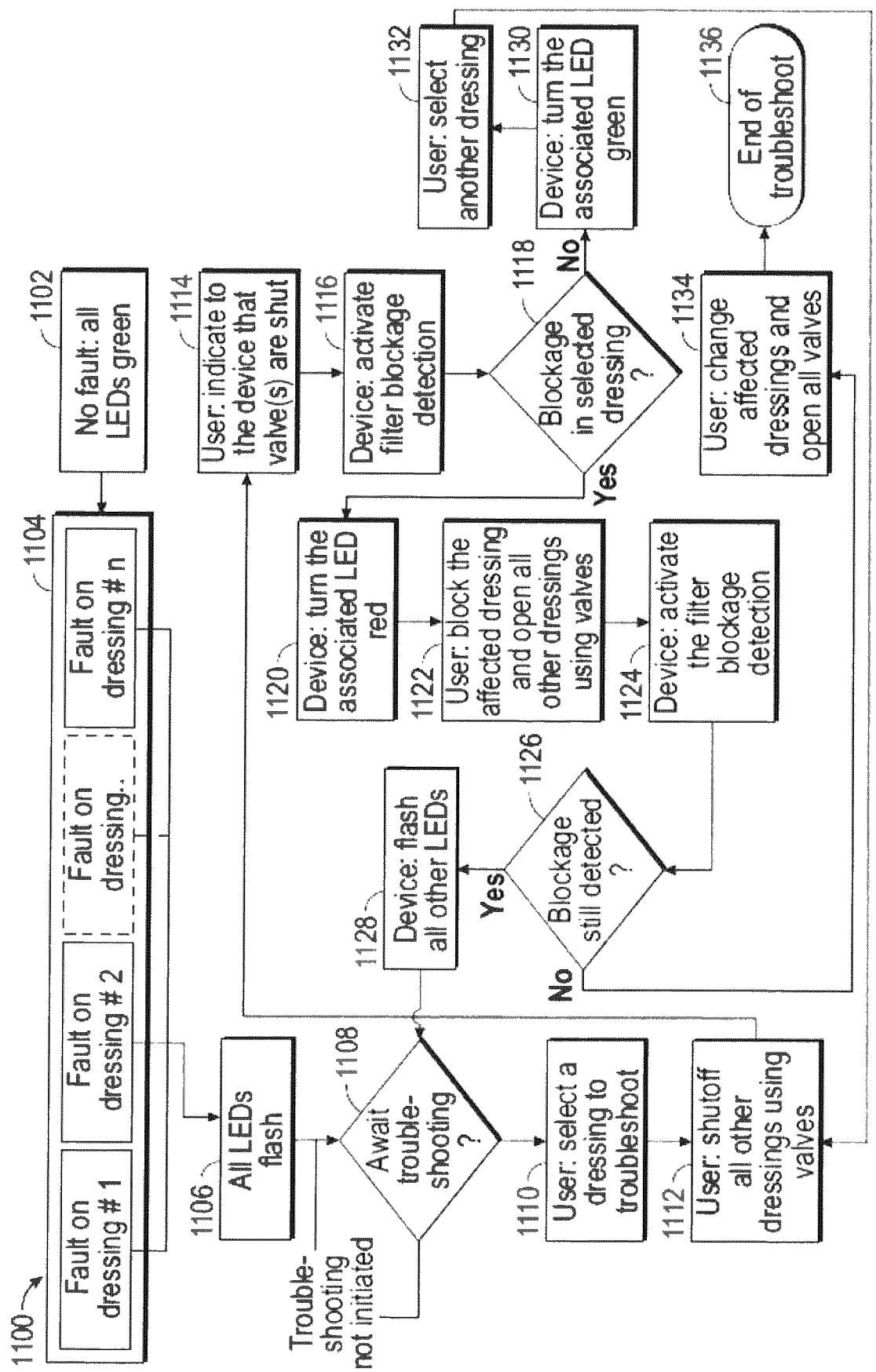
FIG. 11 illustrates a diagnostics process performed by a negative pressure wound treatment system according to some embodiments.

FIG. 11 illustrates a diagnostics process 1100 performed by a negative pressure wound treatment system 700 (see FIG. 7) according to some embodiments. Process 1100 can be performed by a controller of the negative pressure wound treatment system. The process can monitor the measured pressure and can determine whether any of the fluid flow paths/wound dressings in the negative pressure system are experiencing an operating condition.

At block 1102, the process has determined that no operating conditions exist within the negative pressure system. In some examples, one or more LEDs or other indicators can be used to indicate to a user or caregiver that no operating conditions exist. For example, each wound dressing can have a corresponding LED that is ON when no operating condition is detected on the associated wound dressing and OFF when an operating condition is detected on the associated wound dressing (or vice versa). In some examples, when no operating condition is detected in the negative pressure system, all associated LEDs are ON. In some examples, other indicators may be associated with a no fault state (state in which no operating conditions are detected), such as sounds, wireless messages, display notifications and/or other signals which may get the attention of a user or caregiver. In some examples, the TNP apparatus may not provide an indication of no detected operating condition.

In some examples, the process continuously monitors the measured pressure to determine if any of the fluid flow paths/wound dressings within the negative pressure system are experiencing an operating condition. In other examples, the process monitors the measured pressured at predetermined intervals (such as, 1 minute, 2 minutes, 5 minutes, 10 minutes, 15 minutes, 20 minutes, 30 minutes, or 60 minutes). In some instances, the process monitors the pressure sensor responsive to input by a user.

At block 1104, the process determines that an operating condition has occurred. As mentioned above, an operating condition can include a blockage, leakage, overpressure, dressing full condition, or the like. The process can detect one of the foregoing an operating condition conditions by analysing the pressure measured by pressure sensor 502. For example, an operating condition can be determined based on a change in measured pressure (such as, spike, dip, increase, or decrease in measured pressure) or flow rate.

For instance, in a negative pressure system operating in a normal state (for example, where no fluid flow paths/wound dressings are experiencing an operating condition), the pressure sensor measures an "expected pressure," that is, a pressure equivalent (or almost equivalent) to a selected pressure to be supplied by the negative pressure source. In contrast, when the negative pressure system is operating in a state other than normal (such as one or more of the fluid flow paths/wound dressings are experiencing an operating condition), the pressure sensor measures a pressure different from the expected pressure. In some examples, a fluid flow path/wound dressing experiencing a blockage, overpressure, or dressing full condition, can cause the pressure sensor to measure a higher than expected pressure. In other examples, a fluid flow path/wound dressing experiencing a leakage condition can cause the pressure sensor to measure a lower than expected pressure. As described herein, flow rate can be used to determine presence of an operating condition in some implementations.

At block 1106, and upon a determination that a wound dressing within the negative pressure system is experiencing an operating condition, the process can provide indication of a detected operating condition. For instance, each wound dressing can have a corresponding LED. Upon the detection of an operating condition, the process can cause each of the LEDs to flash. In other examples, other indicators are used in place of or in supplement to LEDs. For example, a sound, wireless message, display notification and/or other signal can be used to indicate that the negative pressure system is experiencing an operating condition. In some examples, the process can at least momentarily turn off the negative pressure therapy system to indicate the system is experiencing an operating condition.

At block 1108, the process can suspend or wait to initiate troubleshooting until it receives input from a user. For example, the process can detect that the system is experiencing an operating condition and provide an indication to the user or to a caregiver and wait until the process receives an acknowledgement. In some examples, the process immediately begins troubleshooting without waiting for input from a user or begins troubleshooting after a delay.

At block 1110, a user acknowledges the determination that a fluid flow path/wound dressing within the negative pressure system is experiencing an operating condition and provides input to the process to start troubleshooting. In some instances, the user can press a button to start the troubleshooting process. In other examples, the process automatically starts the troubleshooting process immediately or after a predetermined interval of not receiving input from a user.

The user continues by selecting a fluid flow path/wound dressing to troubleshoot (for example, test for operating conditions). In some examples, the user and/or the process can make this selection. The selection of the fluid flow path/wound dressing can be based on a variety of factors including the user's suspicions, a suggestion by the process, and the like or a fluid flow path/wound dressing can be arbitrarily selection or selected based on an algorithm.

At block 1112, after a fluid flow path/wound dressing has been selected for testing, the valve associated with the selected flow path/dressing is opened and the valve(s) associated with the unselected flow path(s)/dressing(s) are closed, thereby likening the negative therapy system to a negative pressure system having a single wound dressing with a single negative pressure source. In some examples, the valve(s) can be opened or closed manually. In other examples, the valve(s) can operated by a controller. For instance, the controller can wirelessly control the shut-off valves using a wireless transmitter or transceiver configured to communicate with a wireless transceiver or receiver of the valves. In some examples, a wireless transceiver can communicate with each of the valves and is capable of controlling each of the valves individually or as a unit.

At block 1114, the user can indicate to the process that all valves associated with the unselected flow path(s)/dressing(s) are closed. In some examples, the process can communicate with the valves to determine their status, and does not need input from a user. In some examples, such as when the valves are wirelessly controlled by the controller, the process does not wait for input from a user to open to close the valves.

At blocks 1116-1118, the process activates an operating condition detection scheme to determine whether or not the selected fluid flow path/wound dressing is experiencing an operating condition. This analysis is similar to a determination made by a process in a negative pressure system having a single wound dressing with a single negative pressure source. For example, a lower than expected negative pressure (or higher than expected flow) can indicate to that a fluid flow path/wound dressing is experiencing leakage and a higher than expected negative pressure (or lower than expected flow) can indicate that the fluid flow path/wound dressing is experiencing a blockage, overpressure, or dressing full condition. If the process determines that no operating condition is exists, the process moves to block 1130. If the process determines that an operating condition exists, then the process moves to block 1120.

At block 1120, responsive to a determination that the selected fluid flow path/wound dressing is experiencing an operating condition, the process can provide indication to a user. For instance, the process can cause an LED associated with the selected wound dressing to turn ON or OFF.

At block 1122, the valve associated with the selected flow path/dressing (and any valves associated with other flow path(s)/wound dressing(s) previously determined to be experiencing an operating condition) is closed and all other valves are opened. As mentioned above, the valves can be manually opened or closed by a user or the controller. During this step, all known fluid flow path(s)/wound dressing(s) experiencing an operating condition can be closed off from the negative pressure source and only untested fluid flow path(s)/wound dressing(s) can remain in fluidic communication with the negative pressure source.

At block 1124, the process again activates an operating condition detection scheme, this time to determine whether any of the fluid flow path(s)/wound dressing(s) in fluidic communication with the negative pressure source are experiencing an operating condition. For example, the process determines whether the measure pressure substantially matches the expected pressure (or flow substantially matches the expected flow).

At step 1126, if no operating conditions are detected, the process continues to step 1134. If an operating condition is detected, the process continues to step 1128.

At step 1128, and upon a determination that at least one of the unselected or untested in step 1110 fluid flow path(s)/wound dressing(s) are experiencing an operating condition, the process can provide indication to the user. For examples, each wound dressing can have a corresponding LED. Upon the detection of an operating condition, the process can cause each of the LEDs associated with untested wound dressings to flash. In addition, the process can turn OFF each of the LEDs associated with wound dressings determined to be experiencing an operating condition and turn ON each of the LEDs associated with wound dressings determined not to be experiencing an operating condition. The process then returns to step 1108.

At step 1130, the process has determined that the selected fluid flow path/wound dressing is not experiencing an operating condition. The process can provide indication that the selected flow path/wound dressing is not experiencing an operating condition. For instance, the process and turn the associated LED ON (or green). In some examples, however, one of the remaining fluid flow path(s)/wound dressing(s) is experiencing an operating condition.

At step 1132, a new fluid flow path/wound dressing is selected for testing and the process returns to step 1112. The newly selected fluid flow path/wound dressing has not been tested during the current troubleshooting process (for example, has not been selected at block 1110). As mentioned above, the wound dressing selection can be made by the user and/or the process.

At step 1134, no operating conditions are detected on the fluid flow path(s)/wound dressing(s) associated with the open valves. As such, the fluid flow path(s)/wound dressing(s) associated with closed valves have been determined to be experiencing an operating condition. In some embodiments, if the operating condition is a dressing full condition, the wound dressing(s) experiencing the operating condition are replaced and associated valve(s) are opened. In some examples, the user may manually replace the wound dressings. In some examples, the user will know which wound dressings need to be replaced based on an indication by the process (for example, any OFF LED). In some instances, the user determines which wound dressings should be replaced by looking to see which wound dressings are associated with closed valves. In some examples, the wound dressings are replaced without the help of the user.

At step 1136, the diagnostic mode ends. The process can continue to step 1102 and continue to monitor the measured pressure.

In some cases, to aid in the troubleshooting process, a fluid flow path can be blocked, for example, by closing a valve or clamping the fluid flow path. The flow path can be blocked manually by a user or automatically by a negative pressure wound treatment system. By closing a fluid flow path, the diagnostics process performed by the negative pressure wound treatment system can be simplified, for example, by reducing a number of dressing to troubleshoot. In addition or alternatively, closing a fluid flow path may allow a user to replace a dressing without turning off the negative pressure wound treatment system or otherwise stopping delivery of negative pressure to the other wound dressings.

FIGS. 12A-12C illustrate portable negative pressure apparatuses according to some embodiments. As shown, the TNP apparatus 102 can include an outer housing 1210 for containing and/or supporting components of the TNP apparatus 102.

The outer housing 1210 can include a display 1212 which can be designed to provide a user with information (for example, information regarding an operational status of the TNP apparatus 102). In some embodiments, the display 1212 can include one or more indicators, such as icons 1222 (indicating normal operation), 1224 (indicating presence of one or more leaks preventing the apparatus from providing negative pressure wound therapy), 1226 (check dressing), and 1228 (low power reserve), which can alert the user to one or more operating and/or failure conditions of the TNP apparatus 102. The indicators can include icons for alerting the user to normal or proper operating conditions, pump failure, power failure, the condition or voltage level of the batteries, the condition or capacity of a wound dressing, detection of a leak within the dressing or fluid flow pathway between the dressing and the pump assembly, suction blockage, or any other similar or suitable conditions or combinations thereof.

For example, the display 1212 can include a check dressing indicator 1226, which can provide a user with an alert that prompts a user to check the wound dressing(s). In some cases, the alert will ensure that full or substantially full dressing(s) is(are) timely replaced. For example, a timer or reminder, which can be controlled by a processor of the TNP apparatus, can activate the check dressing indicator 1226 after a predetermined period of time. For example, the check dressing indicator can be configured to activate once a day, such as every 24 hours, or over other suitable duration of time. In some cases, a daily reminder might be frequent enough to minimize a risk of wound maceration, but it is not so frequent that it would become a nuisance to the user. In some cases, the check dressing indicator 1226 can be activated at convenient times for a user. For example, the indicator can be activated at the time that fits with the user's daily life, such as when the user is getting dressed, showering, etc. In some cases, the dressing check indicator 1226 (or other indicators 1222, 1224, or 1228) can be reset by a single or double press of a button 1216 or by some other manipulation of the button 1216. For example, the check dressing indicator can deactivate upon the first press of the button 1216, which will pause the TNP apparatus 102. Such press of the button 1216 can signal user's acknowledgment of the check dressing alert. The TNP apparatus 102 can then reinitiate provision of negative pressure on the second press of the button 1216.

In the illustrated embodiment, one or more icons 1222, 1224, 1226, 1228 can be printed directly on the display 1212 of the outer housing 1210. In some embodiments, one or more of the icons 1222, 1224, 1226, 1228 can be provided on a label attached to a portion of the outer housing 1210. One or more of the icons 1222, 1224, 1226, 1228 can be illuminated when the status corresponding to that icon exists in the system.

The TNP apparatus 102 can include one or more user input features, such as the button 1216, designed to receive an input from the user for controlling the operation of the TNP apparatus 102. In the embodiment shown, a single button is present which can be used to activate and deactivate the TNP apparatus 102 and/or control other operating parameters of the TNP apparatus 102. For example, in some embodiments, the button 1216 can be used to activate the TNP apparatus 102, pause the TNP apparatus 102, clear indicators, such as any of icons 1222, 1224, 1226, 1228, and/or be used for any other suitable purpose for controlling an operation of the TNP apparatus 102 (for example, by sequentially pushing on the button 1216). The button can be a push style button that can be positioned on an outside, front surface of the housing 1210. In other embodiments, multiple input features (for example, multiple buttons) can be provided on the TNP apparatus 102.

In some embodiments, the TNP apparatus 102 can include a connector 1202 for connecting a tube or conduit (such as an inlet manifold branching attachment 206 or an integrated inlet manifold) to the TNP apparatus 102. As illustrated in FIG. 12B, the connector 1202 can include two conduits 602 and 604 for fluidically connecting the system to two separate wounds. In some embodiments, more than two wounds can be connected to the TNP apparatus 102 via conduits conduits 602 and 604 or one or more additional conduits.

The system embodiments described herein can have a compact, small size. In some embodiments disclosed herein, a pump assembly of the system can have a diameter (for example, equivalent diameter) or lateral size between 15 mm and 35 mm, less than 15 mm, less than 25 mm, less than 35 mm, or less than 50 mm. For example, in some embodiments, the system can have a diameter or lateral size of 10 mm, 23 mm, or 40 mm, or can have a diameter or lateral size in the range of approximately 26 mm to approximately 27 mm, between approximately 22 mm or smaller and approximately 28 mm. In some embodiments disclosed herein, the system can have a thickness or height of approximately 8 mm, between approximately 6 mm and approximately 10 mm, or a thickness or height of less than 20 mm. For example, in some embodiments, the thickness or height of the system can be 5 mm, 12 mm, or 20 mm.

In some examples, the TNP apparatus 102 can include a negative pressure source configured to apply pressure for up to 7 days, 10 days, 30 days, and the like. The negative pressure source can include a motor, voice coil actuator, piezoelectric actuator, and the like. In some embodiments, the TNP apparatus 102 can be battery powered (for instance, powered off two AA batteries).

In some embodiments, in addition to or instead of the one or more indicators of the display 1212, the apparatus can provide one or more audible, tactile, haptic, or the like alerts.

FIG. 12C illustrates a portable negative pressure apparatus 1210 that incorporates shut-off valves 1242, 1244 (sometimes referred to as a tap) in each fluid flow path according to some embodiments. As described herein with respect to FIG. 4A-4C, 5 or 7, a plurality of shut-off valves 1242, 1244 can be positioned in the negative pressure therapy system such that the closure of a valve blocks provision of negative pressure to an associated wound dressing. The shut-off valves 1242, 1244 can be positioned anywhere in the fluid flow path, such as between the outlets of the inlet manifold branching attachment (e.g., conduits 602 and 604) and a corresponding dressing inlet or, in some cases, on or within the dressing. In some examples, as described herein with respect to FIGS. 4A-C, one or more shut-off valves 1242, 1244 can be integrated into the inlet manifold branching attachment.

In some cases, one or more of the valves 1242, 1244 are manual shut-off valves. For instance, a user can manually close the valve 1242 thereby blocking provision of negative pressure to the associated wound dressing. In other examples, one or more of the valves can be operated by the system. For example, the valves can be electromechanical valves. For instance, a TNP apparatus can communicate with the valves to open and/or close each valve individually or as a unit. The communication between the valves and the TNP apparatus can be wired or wireless. For instance, a wireless transceiver of the TNP apparatus can communicate with a wireless transceiver of the valves.

FIGS. 12A-12G illustrate user interface displays 1212 for a portable negative pressure apparatus according to some embodiments. A display 1212 may have a combination of one or more of any of the indicators 1222, 1224, 1226, 1228 illustrated in FIGS. 12A-12G. However, fewer, more, or different indicators are contemplated. For example, in some cases, a portable negative pressure apparatus may not include a display and/or the display may not include any button or indicators.

Figure 13:
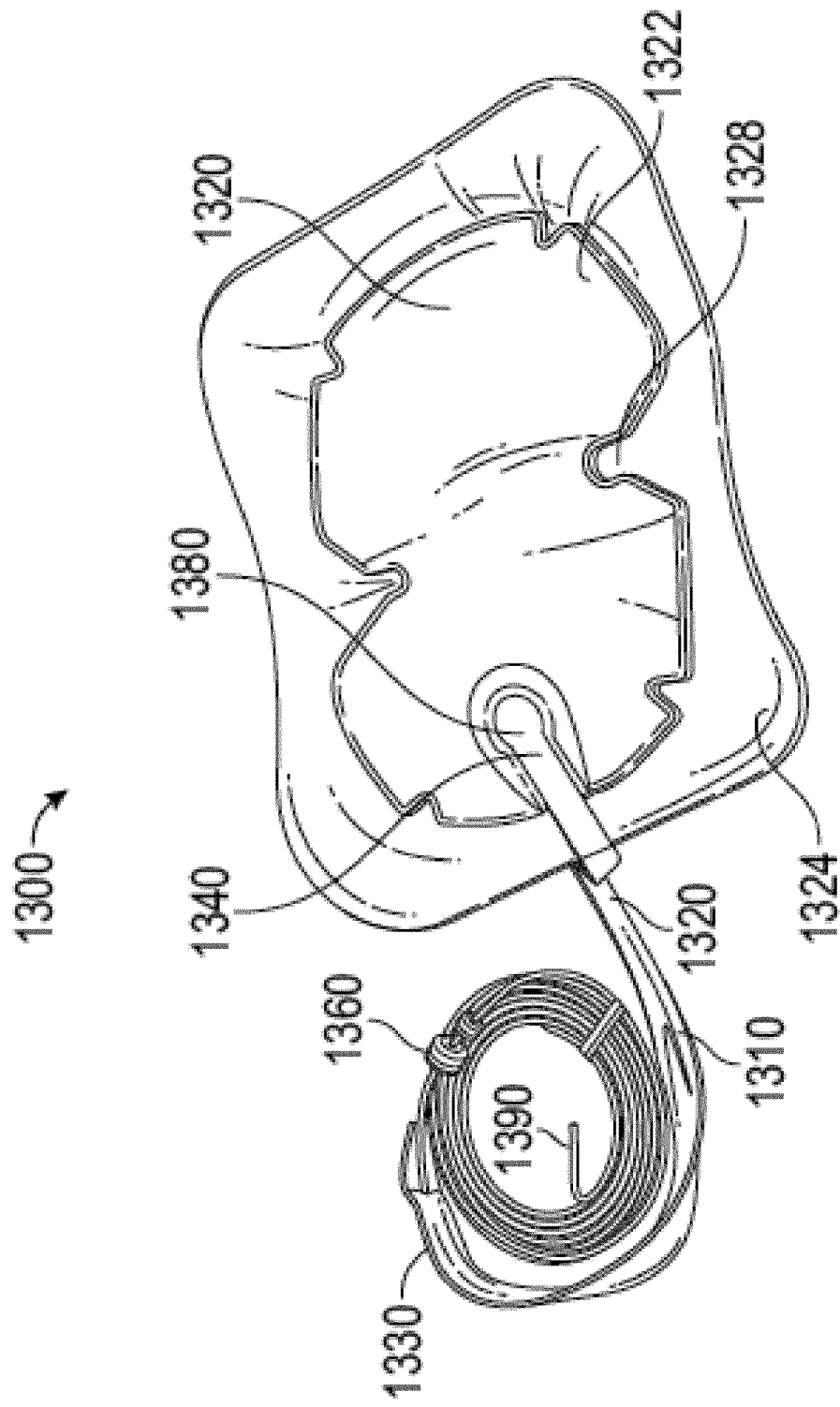
FIG. 13 illustrates a wound dressing according to some embodiments.

FIG. 13 illustrates a perspective view of an embodiment of a wound dressing 1300 in conjunction with a fluidic connector 1310. The illustrated wound dressing can be used with any of the embodiment of negative pressure systems described herein. As is illustrated, the wound dressing 1300 has an oval shaped absorbent layer 1320 having multiple lobes 1322. In some embodiments, the absorbent layer 1320 can have six lobes. In some examples, two or more lobes 1322 (such as, six lobes) are provided on the wound dressing 1300; the lobes 1322, and specifically, the gaps between the lobes 1322, aid the wound dressing 1300 in conforming to nonplanar wounds. For example, it may be advantageous to use the dressing 1300 to conform around joints such as elbows and knees. The dressing 1300 can have a rectangular or square shaped backing layer 1324, and in some embodiments, the overall dressing 1300 may measure 190 mm×230 mm, or 145.5 mm×4100 mm.

In some examples, the dressing 1300 may also have circular cutouts 1328 in a central-waisted portion, which may be located along a midline of the dressing 1300 transverse to a longitudinal axis of the dressing 1300. Such cutouts 1328 may be, in some embodiments, 10 mm, or approximately 10 mm, in diameter, or may be in the range of 5 mm to 25 mm, or approximately 5 mm to approximately 25 mm, in diameter. As illustrated, the circular cutouts 1328 can be symmetrically arranged on opposite sides of a longitudinal midline of the dressing 1300, and may form an arc of greater than 180 degrees, sometimes between 180 and 270 (or about 180 to 270) degrees.

As illustrated, the fluidic connector 1310 may include an elongate conduit, or a bridge 1320 having a proximal end 1330 and a distal end 1340, and an applicator 1380 at the distal end 1340 of the bridge 1320. In some examples, the bridge 1320 provides a soft, fluidic connection between the tube 1390 and the wound dressing 1300 and can advantageously distance the tube 1390 from wound dressing 1300, thereby reducing the potential for pressure points caused by the tube 1390. In some examples, the length of the bridge 1320 can be 20, 30, 45, 60, or 70 centimeters (+/−a few centimeters). An optional coupling 1360 can be disposed at the proximal end 1330 of the bridge 1320. In some examples, a cap (not shown) can be attached to the coupling 1360 and can be useful in preventing fluids from leaking out of the proximal end 1330.

A negative pressure system (such as the one illustrated in FIGS. 12A-12C) may be connected to the coupling 1360 via a tube 1390 (such as by connecting the tube 1390 to one of the connectors 602 or 604), or the system may be connected directly to the coupling 1360 or directly to the bridge 1320. In use, the dressing 1300 is placed over a suitably prepared wound, which may in some cases be filled with a wound packing material such as foam or gauze. The applicator 1380 of the fluidic connector 1310 has a sealing surface that is placed over an aperture in the dressing 1300 and is sealed to the top surface of the dressing 1300. Either before, during, or after connection of the fluidic connector 1310 to the dressing 1300, a system is connected via the tube 1390 to the coupling 1360, or is connected directly to the coupling 1360 or to the bridge 1320. The system is then activated, thereby supplying negative pressure to the wound. Application of negative pressure may be applied until a desired level of healing of the wound is achieved. In some embodiments, the system can be miniaturized and portable, although larger conventional pumps may also be used with the dressing 1300. In some embodiments, the system may be attached or mounted within, onto, or adjacent the dressing 1300.

In some embodiments, a source of negative pressure (such as a pump) and some or all other components of a TNP system, such as power source(s), sensor(s), connector(s), user interface component(s) (such as button(s), switch(es), speaker(s), etc.) and the like, can be integral with the wound dressing 1300. The wound dressing 1300 can include a cover layer for positioning over the layers of the wound dressing. The cover layer can be the upper most layer of the dressing. In some embodiments, the wound dressing 1300 can include a second cover layer for positioning over the layers of the wound dressing and any of the integrated components. The second cover layer can be the upper most layer of the dressing or can be a separate envelope that encloses the integrated components of the topical negative pressure system.

As shown in FIG. 13, the fluidic connector 1310 includes an enlarged distal end, or head 1340 that is in fluidic communication with the dressing 1300 as will be described in further detail below. In one embodiment, the enlarged distal end has a round or circular shape. The head 1340 is illustrated here as being positioned near an edge of the dressing 1300, but may also be positioned at any location on the dressing. For example, some embodiments may provide for a centrally or off-centered location not on or near an edge or corner of the dressing 1300. In some embodiments, the dressing 1300 may include two or more fluidic connectors 1310, each having one or more heads 1340, in fluidic communication therewith. In an embodiment, the head 1340 may measure 30 mm along its widest edge. The head 1340 forms at least in part the applicator 1380, described above, that is configured to seal against a top surface of the wound dressing.

Figure 14:
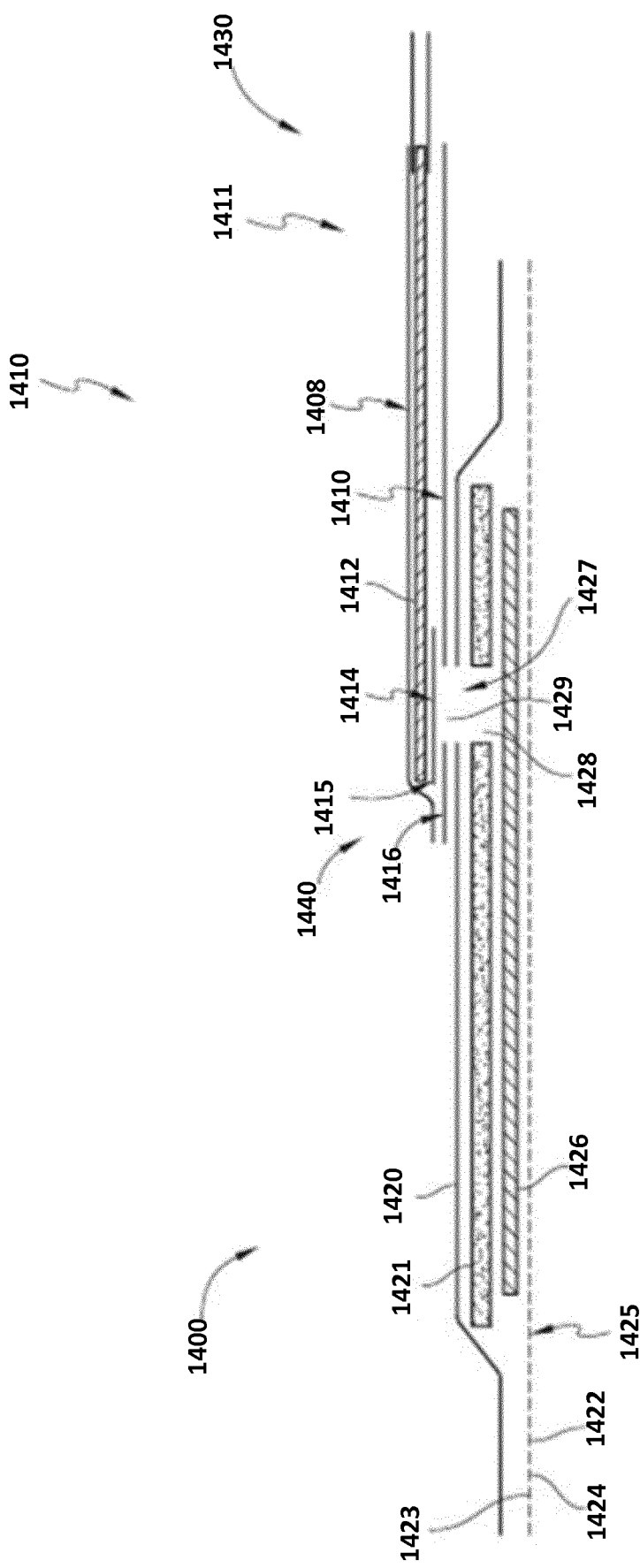
FIG. 14 illustrates a cross section of an embodiment of a fluidic connector connected to a wound dressing.

FIG. 14 illustrates a cross-section through a wound dressing 1400 similar to the wound dressing 1300 as shown in FIG. 13 along with fluidic connector 1410. The wound dressing 1400, which can alternatively be any wound dressing embodiment disclosed herein or any combination of features of any number of wound dressing embodiments disclosed herein, can be located over a wound site to be treated. The dressing 1400 can be used with any of the negative pressure system embodiment described herein. The dressing 1400 may be placed as to form a sealed cavity over the wound site. In an embodiment, the dressing 1400 includes a top or cover layer, or backing layer 1420 attached to an optional wound contact layer 1422, both of which are described in greater detail below. These two layers 1420, 1422 can be joined or sealed together to define an interior space or chamber. This interior space or chamber may include additional structures that may be adapted to distribute or transmit negative pressure, store wound exudate and other fluids removed from the wound, and other functions that will be explained in detail below. Examples of such structures, described below, include a transmission layer 1426 and an absorbent layer 1421.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 14, the wound contact layer 1422 can be a polyurethane layer or polyethylene layer or other flexible layer which is perforated, for example via a hot pin process, laser ablation process, ultrasound process or in some other way or otherwise made permeable to liquid and gas. The wound contact layer 1422 has a lower surface 1424 and an upper surface 1423. The perforations 1425 can include through holes in the wound contact layer 1422 that enable fluid to flow through the layer 1422. The wound contact layer 1422 helps prevent tissue ingrowth into the other material of the wound dressing. The perforations can be small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 1422 may help maintain the integrity of the entire dressing 1400 while also creating an airtight seal around the absorbent pad in order to maintain negative pressure at the wound.

Some embodiments of the wound contact layer 1422 may also act as a carrier for an optional lower and upper adhesive layer (not shown). For example, a lower pressure sensitive adhesive may be provided on the lower surface 1424 of the wound dressing 1400 whilst an upper pressure sensitive adhesive layer may be provided on the upper surface 1423 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 1400 to the skin around a wound site. In some embodiments, the wound contact layer may include perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 1426 of porous material can be located above the wound contact layer 1422. This porous layer, or transmission layer, 1426 allows transmission of fluid including liquid and gas away from a wound site into upper layers of the wound dressing. In particular, the transmission layer 1426 can ensure that an open air channel can be maintained to communicate negative pressure over the wound area even when the absorbent layer has absorbed substantial amounts of exudates. The layer 1426 can remain open under the typical pressures that will be applied during negative pressure wound therapy as described above, so that the whole wound site sees an equalized negative pressure. The layer 1426 may be formed of a material having a three dimensional structure. For example, a knitted or woven spacer fabric (for example Baltex 7970 weft knitted polyester) or a non-woven fabric could be used.

In some embodiments, the transmission layer 1426 includes a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 1421 helps lock the liquid away or itself wicks the liquid onwards towards the cover layer where it can be transpired.

To improve the liquid flow across the transmission layer 1426 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 1421 of absorbent material is provided above the transmission layer 1426. The absorbent material, which includes a foam or non-woven natural or synthetic material, and which may optionally include a super-absorbent material, forms a reservoir for fluid, particularly liquid, removed from the wound site. In some embodiments, the layer 1421 may also aid in drawing fluids towards the backing layer 1420.

The material of the absorbent layer 1421 may also prevent liquid collected in the wound dressing 1400 from flowing freely within the dressing, and can act so as to contain any liquid collected within the dressing. The absorbent layer 1421 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 1421 may typically be manufactured from ALLEVYN™ foam, Freudenberg 114-224-4 and/or Chem-Posite™11C-450. In some embodiments, the absorbent layer 1421 may include a composite having superabsorbent powder, fibrous material such as cellulose, and bonding fibers. In an embodiment, the composite is an airlaid, thermally-bonded composite.

In some embodiments, the absorbent layer 1421 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 1427 can be provided in the backing layer 1420 to allow a negative pressure to be applied to the dressing 1400. The fluidic connector 1410 can be attached or sealed to the top of the backing layer 1420 over the orifice 1427 made into the dressing 1400, and communicates negative pressure through the orifice 1427. A length of tubing may be coupled at a first end to the fluidic connector 1410 and at a second end to a negative pressure system (not shown) to allow fluids to be removed from the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 1410 may be adhered and sealed to the backing layer 1420 using an adhesive such as an acrylic, cyanoacrylate, epoxy, UV curable or hot melt adhesive. The fluidic connector 1410 may be formed from a soft polymer, for example a polyethylene, a polyvinyl chloride, a silicone or polyurethane having a hardness of 30 to 90 on the Shore A scale. In some embodiments, the fluidic connector 1410 may be made from a soft or conformable material.

The absorbent layer 1421 can include at least one through hole 1428 located so as to underlie the fluidic connector 1410. The through hole 1428 may in some embodiments be the same size as the opening 1427 in the backing layer, or may be bigger or smaller. As illustrated in FIG. 14 a single through hole can be used to produce an opening underlying the fluidic connector 1410. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 1428 can be provided in the absorbent layer 1421 beneath the orifice 1427 such that the orifice is connected directly to the transmission layer 1426 as illustrated in FIG. 14. This allows the negative pressure applied to the fluidic connector 1410 to be communicated to the transmission layer 1426 without passing through the absorbent layer 1421. This ensures that the absorbent layer does not inhibit the negative pressure applied to the wound site as it absorbs wound exudates. In other embodiments, no aperture may be provided in the absorbent layer 1421, or alternatively a plurality of apertures underlying the orifice 1427 may be provided. In further alternative embodiments, additional layers may be provided over the absorbent layer 1421 and beneath the backing layer 1420.

The backing layer 1420 can be gas impermeable, but moisture vapor permeable, and can extend across the width of the wound dressing 1400. The backing layer 1420, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 1420 and a wound site where a negative pressure can be established. The backing layer 1420 can be sealed to the wound contact layer 1422 in a border region around the circumference of the dressing, ensuring that no air is drawn in through the border area, for example via adhesive or welding techniques. The backing layer 1420 protects the wound from external bacterial contamination (bacterial barrier) and allows liquid from wound exudates to be transferred through the layer and evaporated from the film outer surface. The backing layer 1420 can include two layers; a polyurethane film and an adhesive pattern spread onto the film. The polyurethane film can be moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 1421 may be of a greater area than the transmission layer 1426, such that the absorbent layer overlaps the edges of the transmission layer 1426, thereby ensuring that the transmission layer does not contact the backing layer 1420. This provides an outer channel of the absorbent layer 1421 that is in direct contact with the wound contact layer 1422, which aids more rapid absorption of exudates to the absorbent layer. Furthermore, this outer channel ensures that no liquid is able to pool around the circumference of the wound cavity, which could seep through the seal around the perimeter of the dressing leading to the formation of leaks. As illustrated in FIG. 14, the absorbent layer 1421 may define a smaller perimeter than that of the backing layer 1420, such that a boundary or border region is defined between the edge of the absorbent layer 1421 and the edge of the backing layer 1420.

As shown in FIG. 14, one embodiment of the wound dressing 1400 includes an aperture 1428 in the absorbent layer 1421 situated underneath the fluidic connector 1410. In use, for example when negative pressure is applied to the dressing 1400, a wound facing portion of the fluidic connector may thus come into contact with the transmission layer 1426, which can thus aid in transmitting negative pressure to the wound site even when the absorbent layer 1421 is filled with wound fluids. Some embodiments may have the backing layer 1420 be at least partly adhered to the transmission layer 1426. In some embodiments, the aperture 1428 is at least 1-2 mm larger than the diameter of the wound facing portion of the fluidic connector 1410, or the orifice 1427.

In particular for embodiments with a single fluidic connector 1410 and through hole, the fluidic connector 1410 and through hole can be located in an off-center position as illustrated in FIG. 13. Such a location may permit the dressing 1400 to be positioned onto a patient such that the fluidic connector 1410 is raised in relation to the remainder of the dressing 1400. So positioned, the fluidic connector 1410 and the filter 1414 may be less likely to come into contact with wound fluids that could prematurely occlude the filter 1414 so as to impair the transmission of negative pressure to the wound site.

Turning now to the fluidic connector 1410, some embodiments include a sealing surface 1416, a bridge 1411 (corresponding to bridge 1320) in FIG. 13) with a proximal end 1330 and a distal end 1340, and a filter 1414. The sealing surface 1416 can form the applicator previously described that is sealed to the top surface of the wound dressing. In some embodiments a bottom layer of the fluidic connector 1410 may include the sealing surface 1416. The fluidic connector 1410 may further include an upper surface vertically spaced from the sealing surface 1416, which in some embodiments is defined by a separate upper layer of the fluidic connector. In other embodiments the upper surface and the lower surface may be formed from the same piece of material. In some embodiments the sealing surface 1416 may include at least one aperture 1429 therein to communicate with the wound dressing. In some embodiments the filter 1414 may be positioned across the opening 1429 in the sealing surface, and may span the entire opening 1429. The sealing surface 1416 may be configured for sealing the fluidic connector to the cover layer of the wound dressing, and may include an adhesive or weld. In some embodiments, the sealing surface 1416 may be placed over an orifice in the cover layer. In other embodiments, the sealing surface 1416 may be positioned over an orifice in the cover layer and an aperture in the absorbent layer 1420, permitting the fluidic connector 1410 to provide air flow through the transmission layer 1426. In some embodiments, the bridge 1411 may include a first fluid passage 1412 in communication with a source of negative pressure, the first fluid passage 1412 including a porous material, such as a 3D knitted material, which may be the same or different than the porous layer 1426 described previously. The bridge 1411 can be encapsulated by at least one flexible film layer 1408, 1410 having a proximal and distal end and configured to surround the first fluid passage 1412, the distal end of the flexible film being connected to the sealing surface 1416. The filter 1414 is configured to substantially prevent wound exudate from entering the bridge.

Some embodiments may further include an optional second fluid passage positioned above the first fluid passage 1412. For example, some embodiments may provide for an air leak disposed at the proximal end of the top layer 1408 that is configured to provide an air path into the first fluid passage 1412 and dressing 1400.

The fluid passage 1412 can be constructed from a compliant material that is flexible and that also permits fluid to pass through it if the spacer is kinked or folded over. Suitable materials for the fluid passage 1412 include without limitation foams, including open-cell foams such as polyethylene or polyurethane foam, meshes, 3D knitted fabrics, nonwoven materials, and fluid channels. In some embodiments, the fluid passage 1412 may be constructed from materials similar to those described above in relation to the transmission layer 1426. Advantageously, such materials used in the fluid passage 1412 not only permit greater patient comfort, but may also provide greater kink resistance, such that the fluid passage 1412 is still able to transfer fluid from the wound toward the source of negative pressure while being kinked or bent.

In some embodiments, the fluid passage 1412 may include a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure and/or vented air to the wound site, and may also confer a degree of kinking or occlusion resistance to the fluid passage 1412. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may include several layers of material stacked or layered over each other, which may in some cases be useful in preventing the fluid passage 1412 from collapsing under the application of negative pressure. In other embodiments, the wicking fabric used in the fluid passage 1412 may be between 1.5 mm and 6 mm; or the wicking fabric may be between 3 mm and 6 mm thick, and may include either one or several individual layers of wicking fabric. In other embodiments, the fluid passage 1412 may be between 1.2-3 mm thick, for example, thicker than 1.5 mm Some embodiments, for example a suction adapter used with a dressing which retains liquid such as wound exudate, may employ hydrophobic layers in the fluid passage 1412, and only gases may travel through the fluid passage 1412. Additionally, and as described previously, the materials used in the system can be conformable and soft, which may help to avoid pressure ulcers and other complications which may result from a wound treatment system being pressed against the skin of a patient.

The filter element 1414 can be impermeable to liquids, but permeable to gases, and is provided to act as a liquid bather and to ensure that no liquids are able to escape from the wound dressing 1400. The filter element 1414 may also function as a bacterial barrier. Typically the pore size is 0.2 μm. Suitable materials for the filter material of the filter element 1414 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids, an oleophobic filter membrane can be used, for example 1.0 micron MMT-332 prior to 0.2 micron MMT-323. This prevents the lipids from blocking the hydrophobic filter. The filter element can be attached or sealed to the port and/or the cover film over the orifice. For example, the filter element 1414 may be molded into the fluidic connector 1410, or may be adhered to one or both of the top of the cover layer and bottom of the suction adapter 1410 using an adhesive such as, but not limited to, a UV cured adhesive.

It will be understood that other types of material could be used for the filter element 1414. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the present disclosure, filter element 1414 includes a support layer and an acrylic co-polymer membrane formed on the support layer. The wound dressing 1400 according to certain embodiments of the present disclosure can use microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 1414 may also include an odor absorbent material, for example activated charcoal, carbon fiber cloth or Vitec Carbotec-RT Q2003073 foam, or the like. For example, an odor absorbent material may form a layer of the filter element 1414 or may be sandwiched between microporous hydrophobic membranes within the filter element. The filter element 1414 thus enables gas to be exhausted through the orifice. Liquid, particulates and pathogens however are contained in the dressing.

Similar to the embodiments of wound dressings described above, some wound dressings include a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lays a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that includes a liquid-impermeable, gas-permeable semi-permeable membrane (SPM) or filter that overlies the aforementioned apertures.

Figure 15A:
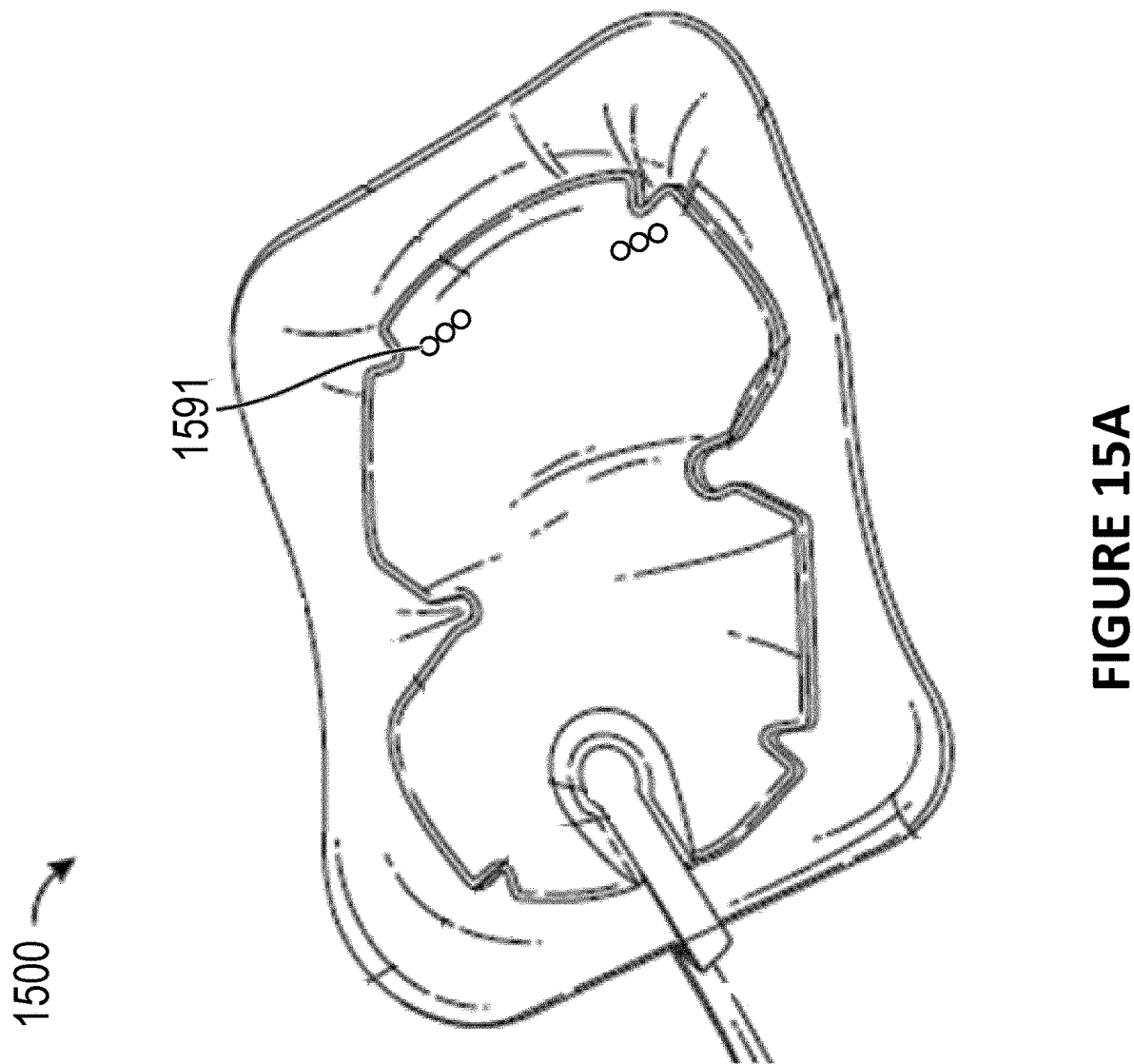
FIGS. 15A-15D illustrate embodiments of a wound dressing incorporating negative pressure indicators according to some embodiments.

FIGS. 15A-15D illustrate embodiments of a wound dressing incorporating negative pressure indicators according to some embodiments. FIG. 15A illustrates negative pressure indicators 1591 on or within the wound dressing 1500 to indicate when negative pressure is established under the dressing. The negative pressure indicator 1591 can be a mechanical indicator. In some embodiments, the negative pressure indicator 1591 can be an indicator that does not require direct line of sight from the patient. For example, the negative pressure indicator 1591 can be an indicator that can be touched or felt by a patient or user. The negative pressure indicator 1591 can be one or more apertures or cut outs in an absorbent material of the dressing. In some cases, once negative pressure is applied under a cover layer, the dressing can tighten and the cover layer can compress as it sucks down into the one or more apertures or cut outs in the absorbent material.

In some embodiments, the negative pressure indicators 1591 can be a small hole array as illustrated in FIG. 15A. In some embodiments, there can be three small holes in the dressing. In some embodiments, two sets of three small hole arrays can be used on opposite sides of the dressing extending longitudinally along the side edges of the dressing as shown in FIG. 15A. In some embodiments, an individual negative pressure indicator can be about 4 mm to about 5 mm in diameter.

The negative pressure indicators can be formed from different types of step changes or indentations created in the dressing as a result of a cut out or hole in the absorbent layer. In some embodiments, the negative pressure indicators can be formed from the hole or cut out in the absorbent material with the cover layer covering the hole or cut out. In some embodiments, the hole or cut out in the absorbent material can be circular, rectangular, triangular, oval, or any other shape. When no vacuum is applied the area can feel loose, whilst under negative pressure the area can tighten and the stepped topography or indentation in the cover layer can be apparent. The stepped topography can be visualized and/or felt by the user. A small hole in the absorbent material as illustrated in FIG. 15A can be used. In other embodiments, a large hole in the absorbent material coupled with another film material or a rectangular strip in the absorbent material coupled with another film material can be used.

Figure 15B:
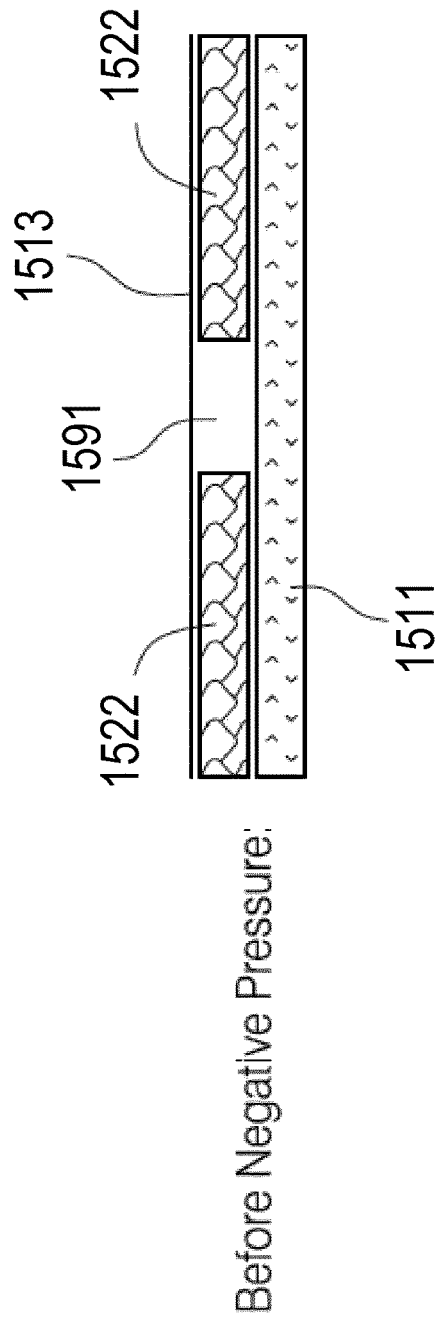
Figure 15C:
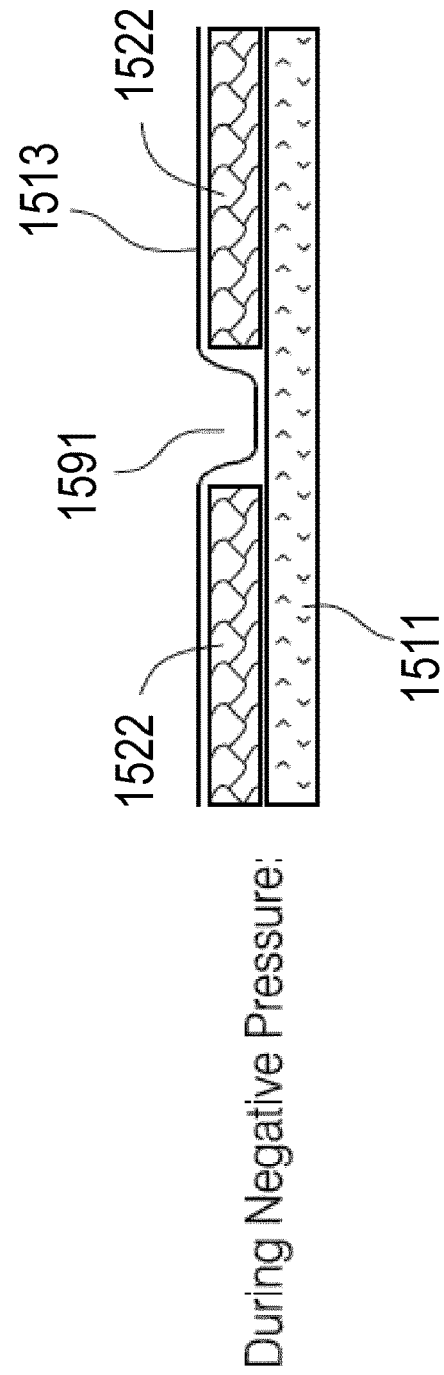

The small hole cut in the absorbent material can be used in combination with the adhesive coated top film. The interaction between the two behave as described previously. Under pressure the absorbent material compresses and the film tightens revealing a film covered hole. This hole can be felt when the system is under negative pressure. When the system returns to ambient pressure, the film "relaxes" or "springs" back to its original state and the hole cannot be as easily felt through the top film material. FIGS. 15B-15C illustrate cross sectional views of the holes before (FIG. 15B) and during (FIG. 15C) negative pressure application. The small hole (about 4 mm to about 5 mm in diameter) negative pressure indicators can allow for a tight step change topography when negative pressure is applied whilst hiding the stepped hole area when the dressing is returned to ambient pressure.

In other embodiments, a large hole with a non-adhesive film can be used as a negative pressure indicator. The large hole can be an aperture or cut out as described with the small holes. However, since the cover layer can be coated with an adhesive material, a non-adhesive film 1592 can be used within the large hole in the absorbent material 1522 to prevent the cover layer 1513 from remaining fixed to the lower layers of the dressing after the cover layer 1513 has been compressed down into the large hole and then returned to ambient pressure.

Figure 15D:
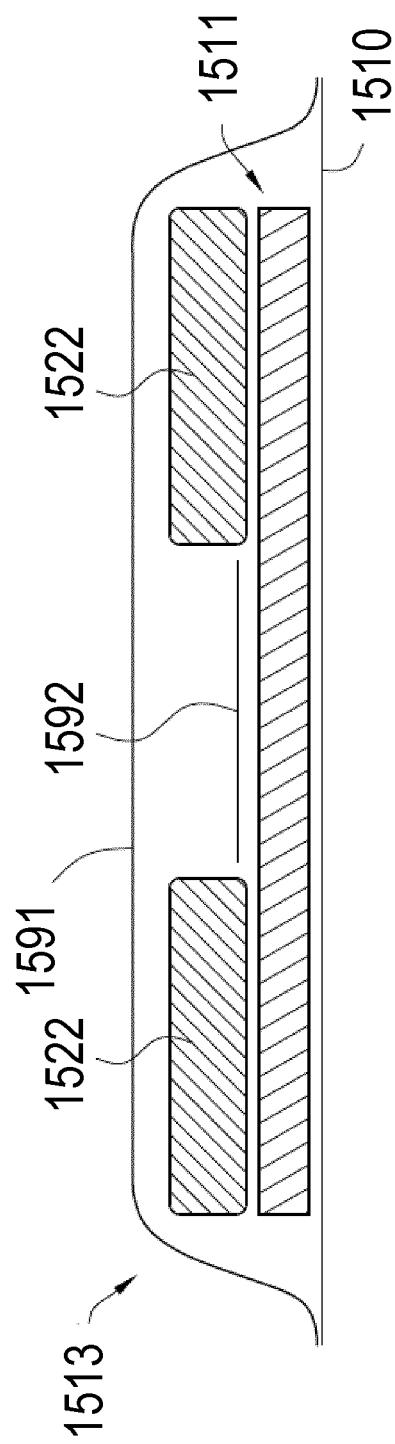

FIG. 15D illustrates a cross sectional view of an embodiment of a wound dressing with a negative pressure indicator 1591 with a large hole aperture in the absorbent material 1522. When the system is under negative pressure, the cover layer 1513 can stick to the non-adhesive film material 1592 and tighten around the absorbent material 1522 creating the step change topography in the dressing defining the negative pressure indicator 1591. Once the dressing returns to ambient pressure, the cover layer 1513 can relax back to its original state. In some embodiments, the large hole can be a circular hole of 12 mm (about 12 mm) in diameter. In some embodiments, more than one large hole can be used. In some embodiments, an array of large holes can be used. In some embodiments, the holes can be less than 3 mm, 3 mm (about 3 mm), 4 mm (about 4 mm), 5 mm (about 5 mm), 6 mm (about 6 mm), 7 mm (about 7 mm), or greater than 7 mm in diameter.

Terminology

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware.

While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A method of determining a blockage in a negative pressure wound therapy system, the method comprising, by a controller:

receiving first pressure data indicative of a combined pressure in a plurality of fluid flow paths fluidically connecting a negative pressure source with a plurality of wound dressings, wherein the plurality of fluid flow paths comprises at least a first fluid flow path including a first valve and a second fluid flow path including a second valve;

based on a determination that the first pressure data satisfies a first blockage threshold, determining that the plurality of fluid flow paths includes a fluid flow path associated with a blockage condition; and based at least in part on a second pressure data, identifying at least one fluid flow path of the plurality of fluid flow paths that is associated with the blockage condition, wherein the second pressure data is obtained when at least one of the first valve or the second valve is closed.

2. The method of claim 1, wherein the first blockage threshold corresponds to an expected combined negative pressure of the plurality of fluid flow paths when at least one of the plurality of fluid flow paths is associated with the blockage condition.

3. The method of claim 1, wherein said identifying comprises:
causing the second valve to be closed; and
determining that the first fluid flow path is associated with the blockage condition based at least in part on determining that the second pressure data obtained when the first valve is open and the second valve is closed satisfies a second blockage threshold.

4. The method of claim 3, wherein the second blockage threshold corresponds to an expected negative pressure of a single fluid flow path that is not associated with the blockage condition.

5. The method of claim 1, further comprising, by the controller:
causing the second valve to be opened;
causing the first valve to be closed; and
determining that the second fluid flow path is associated with the blockage condition based at least in part on determining that a third pressure data obtained when the second valve is open and the first valve is closed satisfies a second blockage threshold.

6. The method of claim 5, wherein the second blockage threshold corresponds to an expected negative pressure of a single fluid flow path that is not associated with the blockage condition.

7. The method of claim 1, wherein the plurality of fluid flow paths further comprises a third fluid flow path including a third valve, wherein the second pressure data is obtained when the first valve is open, the second valve is closed, and the third valve is closed, and wherein said identifying comprises determining that the first fluid flow path is associated with the blockage condition based at least in part on the second pressure data.

8. The method of claim 1, further comprising, by the controller:
while the first valve remains open, cause the second valve to be closed; and
determine that the first fluid flow path is associated with the blockage condition based at least in part on a determination that the second pressure data measured when the first valve is open and the second valve is closed satisfies a second blockage threshold.

9. The method of claim 1, further comprising, by the controller:
determining that the second fluid flow path is not associated with the blockage condition based at least in part on a determination that the second pressure data measured when the second valve is open and the first valve is closed does not satisfy a second blockage threshold, wherein the second blockage threshold corresponds to an expected negative pressure of a single fluid flow path that is not associated with the blockage condition.

10. The method of claim 1, wherein the plurality of fluid flow paths further comprises a third fluid flow path configured to fluidically connect a third wound dressing to the negative pressure source, the third fluid flow path including a third valve, wherein when open the third valve allows passage of fluid through the third fluid flow path, and wherein when closed the third valve blocks passage of fluid through the third fluid flow path.

11. The method of claim 10, wherein the second pressure data is measured when the first valve is open, the second valve is closed, and the third valve is closed, and wherein the identifying the at least one fluid flow path comprises determining that the first fluid flow path is associated with the blockage condition based at least in part on the second pressure data.

12. The method of claim 10, further comprising, by the controller:
while the first valve remains open:
causing the second valve to be closed;
causing the third valve to be closed; and
determining that the first fluid flow path is associated with the blockage condition based at least in part on a determination that the second pressure data measured when the first valve is open and the second and third valves are closed satisfies a second blockage threshold, wherein the second blockage threshold corresponds to an expected negative pressure of a single fluid flow path.

13. The method of claim 12, further comprising, by the controller:
causing the first valve to be closed;
causing the second and third valves to be opened; and
determining that at least one of the second fluid flow path or the third fluid flow path is associated with the blockage condition based at least in part on a third pressure data measured when the first valve is closed and the second and third valves are open.

14. The method of claim 13, further comprising, by the controller:
while first valve remains closed and the second valve remains opened:
causing the third valve to be closed; and
determining that the third fluid flow path is associated with the blockage condition based at least in part on a fourth pressure data measured when the first and second valves are closed and the third valve is open.

15. A method of operating a negative pressure wound therapy device, the method comprising:
responsive to determining that a first pressure indicative of a combined pressure in a first fluid flow path configured to provide a fluidic connection between a negative pressure source and a first wound dressing and a second fluid flow path configured to provide a fluidic connection between the negative pressure source and a second wound dressing satisfies a blockage threshold:
closing a first valve associated with the first fluid flow path, wherein closing the first valve blocks flow of fluid in the first fluid flow path;
opening a second valve associated with the second fluid flow path, wherein opening the second valve allows flow of fluid in the second fluid flow path;
determining an operating condition associated with the second fluid flow path based at least in part on a second pressure indicative of pressure in the second fluid flow path; and
providing indication of the operating condition, wherein the method is performed under control of a controller of the device.

16. The method of claim 15, wherein the operating condition associated with the second fluid flow path comprises blockage in the second fluid flow path.

17. The method of claim 15, further comprising, in response to determining blockage in the second fluid flow path:
- closing the second valve and opening the first valve; and
- providing an indication to replace the second wound dressing.

18. The method of claim 15, further comprising a third fluid flow path configured to provide a fluidic connection between the negative pressure source and a third wound dressing, the third fluid flow path comprising a third valve.

19. A method of operating a negative pressure wound therapy system, the method comprising, by a controller:
- responsive to determining that a first pressure indicative of a combined pressure in a first fluid flow path configured to provide a fluidic connection between a negative pressure source and a first wound dressing, a second fluid flow path configured to provide a fluidic connection between the negative pressure source and a second wound dressing, and a third flow path configured to provide a fluidic connection between the negative pressure source and a third wound dressing satisfies a blockage threshold:
- opening a first valve associated with a first fluid flow path, wherein opening the first valve allows fluid flow in the first fluid flow path;
- closing a second valve associated with a second fluid flow path, wherein closing the second valve blocks fluid flow in the second fluid flow path;
- closing a third valve associated with a third fluid flow path, wherein closing the third valve blocks fluid flow in the third fluid flow path; and
- determining presence of a blockage in the first fluid flow path based at least in part on a second pressure in the first fluid flow path;
- in response to determining that there is the blockage in the first fluid flow path:
  - closing the first valve, wherein closing the first valve blocks fluid flow in the first fluid flow path,
  - opening the second and third valves, wherein opening the second and third valves allows fluid flow in the second and third fluid flow paths,
  - determining presence of a blockage in at least one of the second or third fluid flow paths,
  - in response to determining that there is no blockage in the second and third fluid flow paths, providing a first indication to a user to replace the first wound dressing, and
  - in response to determining that there is blockage in at least one of the second or third fluid flow paths, provide a second indication to the user wherein the method is performed under control of a controller of the system.

20. The method of claim 18, further comprising closing the third valve associated with the third fluid flow path, wherein closing the third valve blocks flow of fluid in the third fluid flow path.

* * * * *

UNITED STATES PATENT AND TRADEMARK OFFICE
CERTIFICATE OF CORRECTION

PATENT NO. : 11,833,014 B2
APPLICATION NO. : 17/498501
DATED : December 5, 2023
INVENTOR(S) : Victoria Beadle It is certified that error appears in the above-identified patent and that said Letters Patent is hereby corrected as shown below:

In the Specification

Column 9, Line 31, delete "mmHg" and insert -- mmHg. --.

Column 9, Line 33, delete "mmHg" and insert -- mmHg. --.

Column 26, Line 28, delete "FIG." and insert -- FIGS. --.

Column 34, Line 1, delete "mm" and insert -- mm. --.

Column 34, Line 12, delete "bather" and insert -- barrier --.

In the Claims

Column 42, Line 24, Claim 19, delete "user" and insert -- user, --.

Signed and Sealed this
Twenty-third Day of January, 2024

Katherine Kelly Vidal
*Director of the United States Patent and Trademark Office*